(12) United States Patent
Church et al.

(10) Patent No.: US 12,264,358 B2
(45) Date of Patent: Apr. 1, 2025

(54) METHOD OF SELECTIVELY SEQUENCING AMPLICONS IN A BIOLOGICAL SAMPLE

(71) Applicant: President and Fellows of Harvard College, Cambridge, MA (US)

(72) Inventors: George M. Church, Brookline, MA (US); Jehyuk Lee, Allston, MA (US); Richard C. Terry, Carlisle, MA (US); Evan R. Daugharthy, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 18/652,923

(22) Filed: May 2, 2024

(65) Prior Publication Data

US 2024/0287582 A1    Aug. 29, 2024

Related U.S. Application Data

(63) Continuation of application No. 17/708,050, filed on Mar. 30, 2022, which is a continuation of application No. 17/363,097, filed on Jun. 30, 2021, now Pat. No. 11,299,767, which is a continuation of application No. 16/157,243, filed on Oct. 11, 2018, now Pat. No. 11,078,520, which is a continuation of application No. 14/774,282, filed as application No.
(Continued)

(51) Int. Cl.
| | | |
|---|---|---|
| *C12Q 1/6806* | (2018.01) | |
| *C12P 19/34* | (2006.01) | |
| *C12Q 1/6844* | (2018.01) | |
| *C12Q 1/6869* | (2018.01) | |
| *C12Q 1/6874* | (2018.01) | |

(52) U.S. Cl.
CPC ........... *C12Q 1/6806* (2013.01); *C12P 19/34* (2013.01); *C12Q 1/6844* (2013.01); *C12Q 1/6869* (2013.01); *C12Q 1/6874* (2013.01)

(58) Field of Classification Search
CPC ...... C12P 19/34; C12Q 1/6844; C12Q 1/6806
See application file for complete search history.

(56) References Cited

U.S. PATENT DOCUMENTS

| | | | |
|---|---|---|---|
| 4,123,610 | A | 10/1978 | Summerton et al. |
| 4,844,617 | A | 7/1989 | Kelderman et al. |
| 4,886,741 | A | 12/1989 | Schwartz |

(Continued)

FOREIGN PATENT DOCUMENTS

| | | |
|---|---|---|
| BR | 112015013784 A2 | 7/2017 |
| BR | 112015013785 A2 | 7/2017 |

(Continued)

OTHER PUBLICATIONS

Weibrecht, I. et al In situ detection of individual mRNA molecules and protein complexes or post-translational modifications using padlock probes combined with the in situ proximity ligation assay (2013) Nature Protocols 8(2): 355-372 (Year: 2013).*

(Continued)

*Primary Examiner* — Samuel C Woolwine
*Assistant Examiner* — Lisa Horth
(74) *Attorney, Agent, or Firm* — Banner & Witcoff, Ltd.

(57) ABSTRACT

Methods of selectively sequencing amplicons in a biological sample are provided.

29 Claims, 10 Drawing Sheets
Specification includes a Sequence Listing.

Related U.S. Application Data

PCT/US2014/018580 on Feb. 26, 2014, now Pat. No. 10,138,509.

(60) Provisional application No. 61/777,383, filed on Mar. 12, 2013.

(56) References Cited

U.S. PATENT DOCUMENTS

| | | |
|---|---|---|
| 4,981,985 A | 1/1991 | Kaplan et al. |
| 5,151,189 A | 9/1992 | Hu et al. |
| 5,424,413 A | 6/1995 | Hogan et al. |
| 5,563,056 A | 10/1996 | Swan et al. |
| 5,594,235 A | 1/1997 | Lee |
| 5,635,352 A | 6/1997 | Urdea et al. |
| 5,695,940 A | 12/1997 | Drmanac et al. |
| 5,830,708 A | 11/1998 | Naughton |
| 5,834,758 A | 11/1998 | Trulson et al. |
| 5,871,921 A | 2/1999 | Landegren et al. |
| 6,068,979 A | 5/2000 | Akhavan-Tafti |
| 6,083,726 A | 7/2000 | Mills, Jr. et al. |
| 6,194,148 B1 | 2/2001 | Hori et al. |
| 6,232,067 B1 | 5/2001 | Hunkapiller et al. |
| 6,306,597 B1 | 10/2001 | Macevicz |
| 6,534,266 B1 | 3/2003 | Singer |
| 6,586,176 B1 | 7/2003 | Trnovsky et al. |
| 6,632,655 B1 | 10/2003 | Mehta et al. |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,745,129 B1 | 6/2010 | Schatz |
| 7,771,949 B2 | 8/2010 | Kramer |
| 7,906,285 B2 | 3/2011 | Drmanac |
| 7,910,304 B2 | 3/2011 | Drmanac |
| 7,941,279 B2 | 5/2011 | Hwang et al. |
| 7,989,166 B2 | 8/2011 | Koch et al. |
| 8,013,134 B2 | 9/2011 | Fredriksson |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,329,404 B2 | 12/2012 | McKernan et al. |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,501,459 B2 | 8/2013 | Chen et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,697,359 B1 | 4/2014 | Zhang |
| 8,871,445 B2 | 10/2014 | Cong et al. |
| 8,906,616 B2 | 12/2014 | Zhang et al. |
| 8,932,814 B2 | 1/2015 | Cong et al. |
| 8,946,389 B2 | 2/2015 | Gao et al. |
| 8,986,926 B2 | 3/2015 | Ferree et al. |
| 8,993,233 B2 | 3/2015 | Zhang et al. |
| 8,999,641 B2 | 4/2015 | Zhang et al. |
| 9,017,992 B2 | 4/2015 | Winther et al. |
| 9,201,063 B2 | 12/2015 | Sood et al. |
| 9,217,151 B2 | 12/2015 | Yin et al. |
| 9,257,135 B2 | 2/2016 | Ong et al. |
| 9,267,135 B2 | 2/2016 | Church et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,541,504 B2 | 1/2017 | Hoyt |
| 9,551,032 B2 | 1/2017 | Landegren et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,896,720 B2 | 2/2018 | Raj et al. |
| 9,909,167 B2 | 3/2018 | Samusik et al. |
| 10,030,261 B2 | 7/2018 | Frisen et al. |
| 10,032,064 B2 | 7/2018 | Hoyt |
| 10,126,242 B2 | 11/2018 | Miller et al. |
| 10,138,509 B2 | 11/2018 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisen et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,844,426 B2 | 11/2020 | Daugharthy et al. |
| 10,872,679 B2 | 12/2020 | Cai et al. |
| 10,964,001 B2 | 3/2021 | Miller |
| 11,021,737 B2 | 6/2021 | Church et al. |
| 11,078,520 B2 | 8/2021 | Church et al. |
| 11,111,521 B2 | 9/2021 | Church et al. |
| 11,118,220 B2 | 9/2021 | Daugharthy et al. |
| 11,293,051 B2 | 4/2022 | Church et al. |
| 11,293,052 B2 | 4/2022 | Church et al. |
| 11,293,054 B2 | 4/2022 | Levner et al. |
| 11,566,277 B2 | 1/2023 | Church et al. |
| 11,639,518 B2 | 5/2023 | Church et al. |
| 2002/0015952 A1 | 2/2002 | Anderson et al. |
| 2002/0029979 A1 | 3/2002 | Freund et al. |
| 2002/0155989 A1 | 10/2002 | Efimov et al. |
| 2002/0172950 A1 | 11/2002 | Kenny et al. |
| 2003/0148335 A1 | 8/2003 | Shen et al. |
| 2003/0165852 A1 | 9/2003 | Schueler et al. |
| 2004/0077014 A1 | 4/2004 | Becker |
| 2004/0081979 A1 | 4/2004 | Knezevic et al. |
| 2004/0248144 A1 | 12/2004 | Mir |
| 2004/0259190 A1 | 12/2004 | Naughton |
| 2005/0064435 A1 | 3/2005 | Su et al. |
| 2005/0106629 A1 | 5/2005 | McGrath et al. |
| 2005/0147981 A1 | 7/2005 | Yamakawa et al. |
| 2005/0191687 A1 | 9/2005 | Wang et al. |
| 2005/0233318 A1 | 10/2005 | Chee et al. |
| 2006/0024711 A1 | 2/2006 | Lapidus et al. |
| 2006/0077536 A1 | 4/2006 | Bromage et al. |
| 2006/0177833 A1 | 8/2006 | Brenner |
| 2006/0183107 A1 | 8/2006 | Melkonyan et al. |
| 2006/0216339 A1 | 9/2006 | Ambron et al. |
| 2006/0228733 A1 | 10/2006 | Pierce et al. |
| 2006/0234261 A1 | 10/2006 | Pierce et al. |
| 2006/0248349 A1 | 11/2006 | Rathjen et al. |
| 2006/0292611 A1 | 12/2006 | Berka et al. |
| 2007/0020650 A1 | 1/2007 | Kahvejian |
| 2007/0087362 A1 | 4/2007 | Church et al. |
| 2007/0117109 A1 | 5/2007 | Rothemund |
| 2007/0117177 A1 | 5/2007 | Luo et al. |
| 2007/0190543 A1 | 8/2007 | Livak |
| 2007/0206275 A1 | 9/2007 | Hemmer et al. |
| 2007/0231823 A1 | 10/2007 | McKernan et al. |

(56) References Cited

U.S. PATENT DOCUMENTS

| | | |
|---|---|---|
| 2007/0292877 A1 | 12/2007 | Dimitrov |
| 2008/0050718 A1 | 2/2008 | Gesteland et al. |
| 2008/0176769 A1 | 7/2008 | Rank et al. |
| 2008/0180790 A1 | 7/2008 | Tafas et al. |
| 2008/0269068 A1 | 10/2008 | Church et al. |
| 2009/0005259 A1 | 1/2009 | Drmanac |
| 2009/0105082 A1 | 4/2009 | Chetverin et al. |
| 2009/0208965 A1 | 8/2009 | Tafas et al. |
| 2009/0220968 A1 | 9/2009 | Issadore et al. |
| 2009/0246879 A1 | 10/2009 | Drmanac et al. |
| 2009/0280559 A1 | 11/2009 | McCarthy |
| 2010/0009868 A1 | 1/2010 | Yan et al. |
| 2010/0047924 A1 | 2/2010 | Webster et al. |
| 2010/0049448 A1 | 2/2010 | Doyle et al. |
| 2010/0076057 A1 | 3/2010 | Sontheimer et al. |
| 2010/0087325 A1 | 4/2010 | Buermann |
| 2010/0151472 A1 | 6/2010 | Nolan et al. |
| 2010/0223276 A1 | 9/2010 | Al-Shameri et al. |
| 2010/0268478 A1 | 10/2010 | Andregg et al. |
| 2011/0020291 A1 | 1/2011 | Banerjee et al. |
| 2011/0033520 A1 | 2/2011 | Mather et al. |
| 2011/0086774 A1 | 4/2011 | Dunaway |
| 2011/0092376 A1 | 4/2011 | Colston, Jr. et al. |
| 2011/0104693 A1 | 5/2011 | Seligmann |
| 2011/0189776 A1 | 8/2011 | Terns et al. |
| 2011/0208040 A1 | 8/2011 | Carmi et al. |
| 2011/0216953 A1 | 9/2011 | Callahan et al. |
| 2011/0223585 A1 | 9/2011 | Gullberg et al. |
| 2011/0223638 A1 | 9/2011 | Wiedenheft et al. |
| 2011/0245111 A1 | 10/2011 | Chee |
| 2011/0257031 A1 | 10/2011 | Bodeau et al. |
| 2011/0294135 A1 | 12/2011 | Carlson |
| 2012/0040397 A1 | 2/2012 | Luo et al. |
| 2012/0122712 A1 | 5/2012 | Goldstein |
| 2012/0126142 A1 | 5/2012 | Matsui et al. |
| 2012/0252686 A1 | 10/2012 | Umbarger et al. |
| 2012/0270214 A1 | 10/2012 | Bernitz et al. |
| 2012/0330636 A1 | 12/2012 | Albou |
| 2013/0017229 A1 | 1/2013 | Mooney et al. |
| 2013/0130248 A1 | 5/2013 | Haurwitz et al. |
| 2013/0245096 A1 | 9/2013 | Abitbol |
| 2013/0253040 A1 | 9/2013 | Miller et al. |
| 2013/0288249 A1 | 10/2013 | Gullberg et al. |
| 2013/0323729 A1 | 12/2013 | Landegren et al. |
| 2014/0049632 A1 | 2/2014 | Hemmer |
| 2014/0068797 A1 | 3/2014 | Doudna et al. |
| 2014/0087378 A1 | 3/2014 | Chatre et al. |
| 2014/0087427 A1 | 3/2014 | Bujnicki et al. |
| 2014/0179006 A1 | 6/2014 | Zhang |
| 2014/0179770 A1 | 6/2014 | Zhang et al. |
| 2014/0200146 A1 | 7/2014 | Xie et al. |
| 2014/0220578 A1 | 8/2014 | Bohannon et al. |
| 2014/0220587 A1 | 8/2014 | Green, Jr. et al. |
| 2014/0270435 A1 | 9/2014 | Dunn |
| 2014/0273226 A1 | 9/2014 | Wu |
| 2014/0273233 A1 | 9/2014 | Chen et al. |
| 2014/0310830 A1 | 10/2014 | Zhang et al. |
| 2014/0315985 A1 | 10/2014 | May et al. |
| 2014/0342457 A1 | 11/2014 | Mali et al. |
| 2015/0004598 A1 | 1/2015 | Gao et al. |
| 2015/0005188 A1 | 1/2015 | Levner et al. |
| 2015/0098126 A1 | 4/2015 | Keller et al. |
| 2015/0133319 A1 | 5/2015 | Fu et al. |
| 2015/0247150 A1 | 9/2015 | Zhang et al. |
| 2015/0267251 A1 | 9/2015 | Cai et al. |
| 2016/0002704 A1 | 1/2016 | Diehl et al. |
| 2016/0024524 A1 | 1/2016 | Joung et al. |
| 2016/0024555 A1 | 1/2016 | Church et al. |
| 2016/0108458 A1 | 4/2016 | Frei et al. |
| 2016/0153006 A1 | 6/2016 | Zhang et al. |
| 2016/0160210 A1 | 6/2016 | Mali et al. |
| 2016/0253584 A1 | 9/2016 | Fodor et al. |
| 2016/0265046 A1 | 9/2016 | Zhang et al. |
| 2016/0289740 A1 | 10/2016 | Fu et al. |
| 2016/0305856 A1 | 10/2016 | Boyden et al. |
| 2016/0340662 A1 | 11/2016 | Zhang et al. |
| 2016/0355795 A1 | 12/2016 | Ran et al. |
| 2016/0358326 A1 | 12/2016 | Sarachan et al. |
| 2016/0376642 A1 | 12/2016 | Landegren et al. |
| 2017/0009278 A1 | 1/2017 | Soderberg et al. |
| 2017/0067096 A1 | 3/2017 | Wassie et al. |
| 2017/0081489 A1 | 3/2017 | Rodriques et al. |
| 2017/0010672 A1 | 4/2017 | Luo et al. |
| 2017/0176338 A1 | 6/2017 | Wu et al. |
| 2017/0191078 A1 | 7/2017 | Zhang et al. |
| 2017/0212983 A1 | 7/2017 | Cai et al. |
| 2017/0220733 A1 | 8/2017 | Zhuang et al. |
| 2017/0253918 A1 | 9/2017 | Kohman |
| 2017/0262984 A1 | 9/2017 | Barnes et al. |
| 2018/0010166 A1 | 1/2018 | Pierce et al. |
| 2018/0051322 A1 | 2/2018 | Church et al. |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0282787 A1 | 10/2018 | Walter et al. |
| 2019/0017106 A1 | 1/2019 | Frisen et al. |
| 2019/0032128 A1 | 1/2019 | Chen et al. |
| 2019/0119735 A1 | 4/2019 | Deisseroth et al. |
| 2019/0203275 A1 | 7/2019 | Frisen et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2020/0010891 A1 | 1/2020 | Beechem et al. |
| 2020/0034347 A1 | 1/2020 | Selly |
| 2020/0090786 A1 | 3/2020 | Quiroz Zarate et al. |
| 2020/0140920 A1 | 5/2020 | Pierce et al. |
| 2020/0239946 A1 | 7/2020 | Dewal |
| 2020/0354782 A1 | 11/2020 | Dewal |
| 2021/0017587 A1 | 1/2021 | Cai et al. |
| 2021/0115504 A1 | 4/2021 | Cai et al. |

FOREIGN PATENT DOCUMENTS

| | | |
|---|---|---|
| BR | 112015008708 A2 | 9/2017 |
| BR | 112015012375 A2 | 9/2017 |
| BR | 112015014425 A2 | 10/2017 |
| BR | 112015022061 A2 | 11/2017 |
| CA | 2891347 A1 | 6/2014 |
| CN | 1580283 A | 2/2005 |
| CN | 1959384 A | 5/2007 |
| CN | 101553306 A | 10/2009 |
| EP | 2878671 A1 | 6/2015 |
| JP | H04-268359 A | 9/1992 |
| JP | 2007-526772 A | 9/2007 |
| JP | 2009-538123 A | 11/2009 |
| JP | 2012-170337 A | 9/2012 |
| JP | 2014-513523 A | 6/2014 |
| JP | 2015-090458 A | 5/2015 |
| KR | 20080003402 A | 1/2008 |
| WO | 9746704 A1 | 12/1997 |
| WO | 98/56955 A1 | 12/1998 |
| WO | 0126708 A1 | 4/2001 |
| WO | 01/37266 A1 | 5/2001 |
| WO | 2003044229 A1 | 5/2003 |
| WO | 2004/104645 A2 | 12/2004 |
| WO | 2006/138257 A2 | 12/2006 |
| WO | 2007/001986 A2 | 1/2007 |
| WO | 2007076128 A2 | 7/2007 |
| WO | 2007086900 A2 | 8/2007 |
| WO | 2007121489 A2 | 10/2007 |
| WO | 2007/123744 A2 | 11/2007 |
| WO | 2007/149696 A1 | 12/2007 |
| WO | 2008069973 A2 | 6/2008 |
| WO | 2008/108989 A2 | 9/2008 |
| WO | 2008157696 A2 | 12/2008 |
| WO | 2009/046348 A1 | 4/2009 |
| WO | 2009046149 A1 | 4/2009 |
| WO | 2010/054108 A2 | 5/2010 |
| WO | 2010080134 A1 | 7/2010 |
| WO | 2010/087325 A1 | 8/2010 |
| WO | 2010104533 A2 | 9/2010 |
| WO | 2011/143124 A2 | 11/2011 |
| WO | 2011143583 A1 | 11/2011 |

(56) References Cited

FOREIGN PATENT DOCUMENTS

| WO | 2012005595 | A2 | | 1/2012 | | |
| WO | 2012058638 | A2 | | 5/2012 | | |
| WO | WO-2012110899 | A2 | * | 8/2012 | ........... | C12Q 1/6809 |
| WO | 2012150035 | A1 | | 11/2012 | | |
| WO | 2012/164565 | A1 | | 12/2012 | | |
| WO | 2013055995 | A2 | | 4/2013 | | |
| WO | 2013096851 | A1 | | 6/2013 | | |
| WO | 2013/098244 | A1 | | 7/2013 | | |
| WO | 2013/126794 | A1 | | 8/2013 | | |
| WO | 2013119827 | A1 | | 8/2013 | | |
| WO | 2013/141680 | A1 | | 9/2013 | | |
| WO | 2013/142578 | A1 | | 9/2013 | | |
| WO | 2013/176772 | A1 | | 11/2013 | | |
| WO | 2014/022702 | A2 | | 2/2014 | | |
| WO | 2014/048083 | A1 | | 4/2014 | | |
| WO | 2014/065596 | A1 | | 5/2014 | | |
| WO | 2014/089290 | A1 | | 6/2014 | | |
| WO | 2014/093595 | A1 | | 6/2014 | | |
| WO | 2014/093622 | A2 | | 6/2014 | | |
| WO | 2014/093661 | A2 | | 6/2014 | | |
| WO | 2014/093694 | A1 | | 6/2014 | | |
| WO | 2014099744 | A1 | | 6/2014 | | |
| WO | 2014/113493 | A1 | | 7/2014 | | |
| WO | 2014/144288 | A1 | | 9/2014 | | |
| WO | 2014/150624 | A1 | | 9/2014 | | |
| WO | 20140163886 | A1 | | 10/2014 | | |
| WO | 2014182528 | A2 | | 11/2014 | | |
| WO | 2014/191518 | A1 | | 12/2014 | | |
| WO | 2014/197568 | A2 | | 12/2014 | | |
| WO | 2015/127183 | A2 | | 8/2015 | | |
| WO | 2015118029 | A1 | | 8/2015 | | |
| WO | 2016007839 | A1 | | 1/2016 | | |
| WO | 2016081740 | A1 | | 5/2016 | | |
| WO | 2017079382 | A1 | | 5/2017 | | |
| WO | 2017079406 | A1 | | 5/2017 | | |
| WO | 2017143155 | A2 | | 8/2017 | | |
| WO | 2017/161251 | A1 | | 9/2017 | | |
| WO | 2017189525 | A1 | | 11/2017 | | |

OTHER PUBLICATIONS

Stougaard, M. et al. In situ detection of non-polyadenylated RNA molecules using turtle probes and target primed rolling circle Prins Bmc Biotch 2007 7:69 1-10 (Year: 2007).*

Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.

Meng Q, Kim DH, Bai X, Bi L, Turro NJ, Ju J. 2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.

Mitra RD, Shendure J, Olejnik J, Edyta Krzymanska O, Church GM. 2003. "Fluorescent in situ sequencing on polymerase colonies" Anal Biochem 320: 55-65.

Porreca GJ, Shendure J, Church GM. 2006. "Polony DNA sequencing" Curr Protoc Mol Biol Chapter 7: Unit 7 8.

Porreca GJ, Zhang K, Li JB, Xie B, Austin D, Vassallo SL, LeProust EM, Peck BJ, Emig CJ, Dahl F, Gao Y, Church GM, Shendure J. 2007. "Multiplex amplification of large sets of human exons" Nat Methods 4: 931-6.

Shendure J, Mitra RD, Varma C, Church GM. 2004. "Advanced sequencing technologies: methods and goals" Nat Rev Genet 5: 335-44.

Shendure JA, Porreca GJ, Church GM. 2008. "Overview of DNA sequencing strategies" Curr Protoc Mol Biol Chapter 7: Unit 7 1.

Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.

Vigneault F, Sismour AM, Church GM. 2008. "Efficient microRNA capture and bar-coding via enzymatic oligonucleotide adenylation" Nat Methods 5: 777-9.

Zhang K, Martiny AC, Reppas NB, Barry KW, Malek J, Chisholm SW, Church GM. 2006. "Sequencing genomes from single cells by polymerase cloning" Nat Biotechnol 24: 680-6.

Zhang K, Zhu J, Shendure J, Porreca GJ, Aach JD, Mitra RD, Church GM. 2006. "Long-range polony haplotyping of individual human chromosome molecules" Nat Genet 38: 382-7.

Church et al.; Center for Casual Consequences of Variation (CCV) "An NHGRI Center for Excellence in Genomic Science" https://web.archive.org/web/20110703211120/http://ccv.med.harvard.edu/; Wayback Machine (Jul. 3, 2011).

Church et al.; Center for Casual Consequences of Variation (CCV) "Our four Specific Aims" https://web.archive.org/web/20110813071548//http://ccv.med.harvard.edu/specific_aims.htm; Wayback Machine (Aug. 13, 2011).

Church; "Proposal for a Center for the determination of the Casual Transcriptional Consequences of Human Genetic Variation (CTCHGV)" http://ccv.med.harvard.edu/CEGS09_Complete_Proposal_minus_Admin_Sections.09May21.final.pdf; Wayback Machine (Aug. 13, 2011).

J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.

May 17, 2021 (US) Notice of Allowance—U.S. Appl. No. 17/122,168.

Jun. 18, 2021 (US) Non-Final Office Action—U.S. Appl. No. 15/772,652.

May 8, 2021—(CN) Office Action—App. No. 201680077501.7.

Jul. 2, 2021—(US) Non-Final Office Action—U.S. Appl. No. 17/238,642.

Jul. 21, 2021 (US) Non-Final Office Action—U.S. Appl. No. 16/693,611.

Ho et al. "Sequencing by ligation variation with endonuclease V digestion and deoxyinosine-containing query oligonucleotides" BMC Genomics, 2011, 12:598.

Jiang et al. "Solar thermal polymerase chain reaction for smartphone-assisted molecular diagnostics" Scientific Reports, 4:4137, 2014.

Ju et al. "Four-color DNA sequencing by synthesis using cleavable fluorescent nucleotide reversible terminators" PNAS, Dec. 26, 2006, vol. 103, No. 52, pp. 19635-19640.

Lubeck et al. "Single cell in situ RNA profiling by sequential hybridization" Nature Methods, Apr. 2014, 11(4), pp. 360-361.

Parinov et al. "DNA sequencing by hybridization to microchip octa- and decanucleotides extended by stacked pentanucleotides" Nucleic Acids Research, 1996, vol. 24, No. 15, pp. 2998-3004.

Schouten et al. "Relative quantification of 40 nucleic acid sequences by multiplex ligation-dependent probe amplification" Nucleic Acids Research, 2002, vol. 30, No. 12, e57.

Jul. 23, 2021 (US) Non-Final Office Action—U.S. Appl. No. 16/170,751.

Aug. 16, 2021—(US) Non-Final Office Action—U.S. Appl. No. 17/363,097.

Guo et al. "Target-driven DNA association to initiate cyclic assembly of hairpins for biosensing and logic gate operation" Chemical Science, 2015, 6, pp. 4318-4323.

Aug. 10, 2021—(GB) Examination Report—App. No. 1904335.5.

Tillberg et al., "Protein-retention expansion microscopy of cells and tissues labeled using standard fluorescent proteins and antibodies," Nat Biotechnol., vol. 34, No. 9, pp. 987-992 (2016).

Chen et al., "Nanoscale imaging of RNA with expansion microscopy," Nature Methods, vol. 13, No. 8, pp. 679-684 (Aug. 1, 2016).

Jul. 6, 2021—(JP) Notice of Reasons for Rejection—App. No. 2019-511929.

Oct. 5, 2021—(EP) Summons to Oral Proceedings—App. No. 17790240.0.

Wang et al. "Rapid and Sensitive Detection of Severe Acute Respiratory Syndrome Coronavirus by Rolling Circle Amplification" Journal of Clinical Microbiology, vol. 43, No. 5, May 2005, pp. 2339-2344.

Nov. 1, 2021—(US) Final Office Action—U.S. Appl. No. 16/830,372.

(56) References Cited

OTHER PUBLICATIONS

Oct. 5, 2021—(JP) Notice of Reasons for Rejection—App. No. 2019-511921.
Goransson et al. "A single molecule array for digital targeted molecular analyses" Nucleic Acids Research, 2009, vol. 37, No. 1, e7, doi:10.1093/nar/gkn921.
Dirks et al. "Triggered amplificaiton by hybridization chain reaction" PNAS; Oct. 26, 2004; vol. 101, No. 43, pp. 15275-15278.
Lubeck et al. "Single cell systems biology by super-resolution imaging and combinatorial labeling" Nature Methods; 9 (7); pp. 743-748; 2012.
Nov. 23, 2021 (US)—Non-Final Office Action—U.S. Appl. No. 17/392,325.
Nov. 30, 2021—(US) Final Office Action—U.S. Appl. No. 15/772,652.
Chen et al. "Functional organization of the human 4D Nucleome" PNAS, vol. 112, No. 26, Jun. 15, 2015, pp. 8002-8007.
Jarvius et al. "Digital quantification using amplified single-molecule detection" Nature Methods, vol. 3, No. 9, Sep. 2006, pp. 725-727.
Jan. 25, 2022—(US) Non-Final Office Action—U.S. Appl. No. 17/266,151.
Dec. 16, 2021—(CN) Office Action—App. No. 201780039335.6.
Jan. 28, 2022—(US) Non-Final Office Action—U.S. Appl. No. 17/366,127.
Dirks et al. "Triggered amplification by hybridization chain reaction" PNAS; Oct. 26, 2004; vol. 101, No. 43, pp. 15275-15278.
Feb. 18, 2022 (US)—Final Office Action—U.S. Appl. No. 16/170,751.
Mar. 4, 2022—(US) Non-Final Office Action—U.S. Appl. No. 17/395,534.
Feb. 8, 2022—(JP) Notice of Reasons for Rejection—App. No. 2021-028931.
Mar. 22, 2022—(US) Final Office Action—U.S. Appl. No. 17/392,325.
Bibikova et al. "Quantitative Gene Expression Profiling in Formalin-Fixed, Paraffin-Embedded Tissues Using Universal Bead Arrays" American Journal of Pathology, vol. 165, No. 5, Nov. 2004.
Capodieci et al. "Gene expression profiling in single cells within tissue" Nature Methods, Sep. 14, 2005, 2(9) pp. 663-665.
Conze et al. "Single molecule analysis of combinatorial splicing" Nucleic Acids Research, Jun. 29, 2010, vol. 38, No. 16; e163.
Femino et al. "Visualization of Single RNA Transcripts in Situ" Science, Apr. 24, 1998, vol. 280, pp. 585-590.
Gavrilovic et al. "Automated Classification of Multicolored Rolling Circle Products in Dual-Channel Wide-Field Fluoescence Microscopy" Cytometry Part A, Jul. 2011, 79(7), pp. 518-527.
Geiss et al. "Direct multiplexed measurement of gene expression with color-coded probe pairs" Nature Biotechnology, vol. 26, No. 3, Mar. 2008, pp. 317-325.
Gunderson et al. "Decoding Randomly Ordered DNA Arrays" Genome Research, May 2004, 14(5), pp. 870-877.
Han et al. "Quantum-dot-tagged microbeads for multiplexed optical coding of biomolecules" Nature Biotechnology, Jul. 2001, vol. 19, No. 7, pp. 631-635.
Itzkovitz et al. "Validating Transcripts with Probes and Imaging Technology" Nature Methods, Apr. 2011, 8(4 Suppl): S12-S19.
Itzkovitz et al. "Single molecule transcript counting of stem cell markers in the mouse intestine" Nat Cell Biol., Nov. 2011, 14(1), pp. 106-114.
Lagunavicius et al. "Novel application of Phi29 DNA polymerase: RNA detection and analysis in vitro and in situ by target RNA-primed RCA" RNA, May 2009, 15(5), pp. 765-771.
Levsky et al. "Fluorescence in situ hybridization: past, present and future" Journal of Cell Science, Jul. 15, 2003, 116 (Pt 14), pp. 2833-2838.
Levsky et al. "Single-Cell Gene Expression Profiling" Science, Aug. 2, 2002, 297(5582), pp. 836-840.
Maierhofer et al. "Multicolor Deconvolution Microscopy of Thick Biological Specimens" American Journal of Pathology, vol. 162, No. 2, Feb. 2003, pp. 373-379.
Meade et al. "Multiplexed DNA detection using spectrally encoded porous SiO2 phtonic crystal particles" Analytical Chemistry, Apr. 1, 2009, 81(7), pp. 2618-2625.

Meade et al. "Multiplexed DNA detection using spectrally encoded porous" Analytical Chemistry, Apr. 1, 2009, 81(7), pp. 2618-2625.
Raj et al. "Imaging individual mRNA molecules using multiple singly labeled probes" Nature Methods, Oct. 2009, 5 (10), pp. 877-879.
Sun et al. "Composite Organic-Inorganic Nanoparticles as Raman Labels for Tissue Analysis" Nano Letters, Feb. 2007, vol. 7, No. 2, pp. 351-356.
Wahlby et al. "Sequential Immunofluorescence Staining and Image Analysis for Detection of Large Numbers of Antigens in Individual Cell Nuclei" Cytometry, Jan. 1, 2002, 47(1), pp. 32-41.
Weibrecht et al. "Simultaneous Visualization of Both Signaling Cascade Activity and End-Point Gene Expression in Single Cells" PLoS One, May 2011, vol. 6, Issue 5, e20148.
Wilson et al. "Encoded Microcarriers For High-Throughput Multiplexed Detection" Angewandte Chemie International Edition, Sep. 18, 2006, 45(37), pp. 6104-6117.
Zhao et al. "Advances of multiplex and high throughput biomolecular detection technologies based on encoding microparticles" Science China Chemistry, Aug. 2011, vol. 54, No. 8, pp. 1185-1201.
Jun. 14, 2022—(US) Non-Final Office Action—U.S. Appl. No. 17/584,959.
Jun. 1, 2022—(EP) Examination Report—App. No. 16862929.3.
Ng et al., "Surface-based mapping of gene expression and probabilistic expression maps in the mouse cortex," Methods, vol. 50, No. 1, pp. 55-62 (Feb. 1, 2010).
Jun. 29, 2022—(US) Non-Final Office Action—U.S. Appl. No. 17/671,803.
Jul. 5, 2022—(JP) Notice of Reasons for Rejection—App. No. 2019-511921.
Leuchowius et al. "Parallel visualization of multiple protein complexes in individual cells in tumor tissue" Molecular & Cellular Proteomics; vol. 12; No. 6; pp. 1563-1571; Jun. 2013; published online Feb. 22, 2013.
Marblestone et al. "Rosetta Brains: A strategy for molecularly-annotated connectomics" arXiv:1404.5103v1-q-bio. NC, https://doi.org/10.48550/arXiv.1404.5103, pp. 1-18; Apr. 21, 2014.
Jul. 21, 2022—(US) Non-Final Office Action—U.S. Appl. No. 16/200,831.
Aug. 25, 2022—(EP) Examination Report—App. No. 17847555.4.
Douse et al. "Multiplexed and Reiterative Fluorescence Labeling via DNA Circuitry" Bioconjug Chem. Dec. 15, 2010;21 (12):2327-31. doi: 10.1021/bc100348q. Epub Nov. 16, 2010.
Douse et al. "Multiplexed and Reiterative Fluorescence Labeling via DNA Circuitry" Bioconjug Chem. Dec. 15, 2010;21 (12):2327-31. doi: 10.1021/bc100348q. Epub Nov. 16, 2010. (Supporting Information).
Choi et al. "Programmable in situ amplification for multiplexed bioimaging" Nature Biotechnology 28: 1208-1212, Oct. 2010, Supplementary Information.
Sep. 15, 2022—(US) Non-Final Office Action—U.S. Appl. No. 16/170,751.
Muller et al. "Towards unlimited colors for fluorescence in-situ hybridization (FISH)" Chromosome Research; 10: 223-232, 2002.
Dec. 5, 2022—(US) Non-Final Office Action—U.S. Appl. No. 17/392,325.
Nov. 21, 2022—(CN) Office Action—Appl No. CN 201780067410.X.
Nov. 23, 2022—(EP) Extended European Search Report—App. No. EP 22170334.1.
Feb. 22, 2023—(CA) Office Action—Appln No. CA 3,022,290.
Chen, et al. "Spatially resolved, highly multiplexed RNA profiling in single cells". Science. Apr. 24, 2015;348(6233): aaa6090, pp. 1-14.
Tam, et al. A microfluidic platform for correlative live-cell and super-resolution microscopy. PloS one. Dec. 29, 2014;9 (12):e115512, pp. 1-20.
Bálint, et al. Correlative live-cell and superresolution microscopy reveals cargo transport dynamics at microtubule intersections. Proceedings of the National Academy of Sciences. Feb. 26, 2013;110(9): pp. 3375-3380.

(56) References Cited

OTHER PUBLICATIONS

Manders, et al. Direct imaging of DNA in living cells reveals the dynamics of chromosome formation. The Journal of cell biology. Mar. 8, 1999;144(5):813-822.
Apr. 6, 2023—(AU) Examination Report—App No. 2016349288.
Aug. 25, 2023—(US) Non-Final Office Action—U.S. Appl. No. 18/064,956.
Nakano et al. "Effects of Molecular Crowding on the Structures, Interactions, and Functions of Nucleic Acids" Chemical Reviews; 2014; 114; pp. 2733-2758.
Al-Attar et al., Clustered Regularly Interspaced Short Palindromic Repeats (CRISPRs ): The Hallmark of an Ingenious Antiviral Defense Mechanism in Prokaryotes, Bioi Chern. (20 11) vol. 392, Issue 4, pp. 277-289.
Carroll, "A Crispr Approach to Gene Targeting" 20(9) Molecular Therapy 1658-1660 (Sep. 2012).
Jinek , et al. 'RNA-programmed genome editing in human cells.' eLite 2013;2:e00471 . retrieved 1-3, 6, 7, 10-12 on Jun. 3, 2014). Retrieved from the Internet. <URL: http://elife.elifesciences.org/content/2/e00471 >. entire document.
Hale et al., Essential Features and Rational Design of CRISPR RNAs That Function With the Cas RAMP Module Complex to Cleave RNAs, Molecular Cell, (20 12) vol. 45, Issue 3, 292-302.
Hatoum-Aslan, et al. 'Mature clustered, regularly interspaced, short palindromic repeats RNA 5,9, 14 (crRNA) length is measured by a ruler mechanism anchored at the precursor processing site.' Proceedings of the National Academy of Sciences. vol. 108, No. 52. pp. 21218-21222. Dec. 2011. entire document.
Makarova et al., "Evolution and classification of the CRISPR-Cas systems" 9(6) Nature Reviews Microbiology 467-477 (1-23) (Jun. 2011).
Rho, Mina et al. 'Diverse CRISPRs Evolving in Human Microbiomes.' PLoS Genetics. vol. 8, No. 6. 1-14 pp. 1-12. Jun. 2012. entire document.
Sontheimer Erik, Project 7: Establishing RNA-Directed DNA Targeting in Eukaryotic Cells; Project dates: Nov. 16, 2011 to Dec. 31, 2012 (Feb. 4, 2012).
Wiedenheft etal., "RNA-guided genetic silencing systems in bacteria and archaea" 482 Nature 331-338 (Feb. 16, 2012).
Liu et al., Cell-Penetrating Peptide-Mediated Delivery of TALEN Proteins via Bioconjugation for Genome Engineering, PLOS ONE, 2014, vol. 9(1), pp. 1-7.
Ramakrishna et al, Gene disruption by cell-penetrating peptide-mediated delivery of Cas9 protein and guide RNA, Genome Res. published online Apr. 2, 2014, pp. 1-20 plus figures.
The Delivery Problem, Nature Biotechnology, 2006, vol. 24(3), pp. 305-306.
Ansari et al., Riboactivators: Transcription activation by non-coding RNA, Grit Rev Biochem Mol Bioi. 2009 ; 44(1 ): 50-61.
Sapranauskas et al (Nucleic Acids Research, 2011, 39:9275-9282).
U.S. Appl. No. 61/794,422, filed Mar. 15, 2013, Davis, G. et al.
U.S. Appl. No. 61/781,598, filed Mar. 14, 2013, Haurwitz, R.
Gilbert, Luke A., et al., "CRISPR-Mediated Modular RNA-Guided Regulation of Transcription in Eukaryotes," Cell, vol. 154, No. 2, Jul. 1, 2013 (Jul. 1, 2013), pp. 442-451.
Mali, P. et al., "Supplementary Materials for RNA-Guided Human Genome Engineering via Cas9," Science, vol. 339, No. 6121, Jan. 3, 2013 (Jan. 3, 2013), pp. 1-36.
Maeder, Morgan L., et al., "Robust, synergistic regulation of human gene expression using TALE activators," HHS Public Access Author Manuscript, vol. 10, No. 3, Feb. 10, 2013 (Feb. 10, 2013), pp. 243-245.
Perez-Pinera, Pablo, et al., "Synergistic and tunable human gene activation by combinations of synthetic transcription factors," Nature Methods, vol. 10. No. 3, Feb. 3, 2013 (Feb. 3, 2013), pp. 239-242.
Preliminary Office Action issued by Brazilian Patent Office on Apr. 7, 2020.
Official Notification issued May 24, 2020 for IL 242959.
Jun. 2, 2020—(JP) Notice of Reasons for Rejection for App. No. 2019-039027.
Jul. 3, 2020—(AU) Examination Report for App. No. 20202039777.
Aug. 19, 2020—(MX) Office Action—App. No. MX/a/2015/016798.
Sep. 10, 2020—(CA) Office Action—App. No. 2,914,638.
Sep. 21, 2020—(NZ) First Examination Report—App. No. 715280.
Sep. 21, 2020—(NZ) First Examination Report—App. No. 753950.
Fu et al., "Improving CRISPR-Cas nuclease specificity using truncated guide RNAs," Nature Biotechnology, vol. 32, pp. 249-284 (Jan. 26, 2014).
Lin et al., "CRISPR/Cas9 systems have off-target activity with insertions or deletions between target DNA and guide RNA sequences," Nucleic Acids Research, vol. 42, No. 11, pp. 7473-7485 (May 16, 2014).
Sep. 21, 2020—(NZ) First Examination Report—App. No. 753951.
Sep. 25, 2020—(RU) Office Action—App. No. 2019114706.
DiCarlo et al., "Genome engineering in Saccharomyces cerevisiae using CRISPR-Cas systems," Nucleic Acids Research, vol. 41, No. 7, pp. 4336-4343 (2013).
Gusev et al. "Rolling Circle Amplification: A New Approach to Increase Sensitivity for Immunohistochemistry and Flow Cyometry" American Journal of Pathology, vol. 159, No. 1, Jul. 2001, pp. 63-69.
Nov. 10, 2020—(US) Non-Final Office Action—U.S. Appl. No. 16/285,292.
Pihlak et al. "Rapid genome sequencing with short universal tiling probes" Nature Biotechnology, vol. 26, No. 6, Jun. 2008, pp. 676-684.
Lizardi "Next-generation sequencing-by-hybridization" Nature Biotechnology, vol. 26, No. 6, Jun. 2008, pp. 649-650.
Mignardi et al. "Fourth-generation sequencing in the cell and the clinic" Genome Medicine, 2014, 6:31.
Dec. 24, 2020 (US)—Notice of Allowance—U.S. Appl. No. 16/393,215.
Terry R, Porreca G, McCarthy K, Church GM. 2008. Polonator Instrument https://web.archive.org/web/20080807155459/http://www.polonator.org/index.htm; Wayback Machine (Aug. 7, 2008) "Open, Affordable, Sequencing . . . ".
Terry R, Porreca G, McCarthy K, Church GM. 2008. Polonator Instrument https://web.archive.org/web/20080807155600/http://www.polonator.org;/vision.aspx; Wayback Machine (Aug. 7, 2008) "The Vision".
Terry R, Porreca G, McCarthy K, Church GM. 2008. Polonator Instrument https://web.archive.org/web/20080807155250/http://www.polonator.org/ecosystem; Wayback Machine (Aug. 7, 2008) "The Polonator Ecosystem".
Terry R, Porreca G, McCarthy K, Church GM. 2008. Polonator Instrument https://web.archive.org/web/20080807155759/http://www.polonator.org/instrument; Wayback Machine (Aug. 7, 2008) "Instrument Overview".
Terry R, Porreca G, McCarthy K, Church GM. 2008. Polonator Instrument https://web.archive.org/web/20080807155857/http://www.polonator.org; Wayback Machine (Aug. 7, 2008) "Protocols".
Terry R, Porreca G, McCarthy K, Church GM. 2008. Polonator Instrument https://web.archive.org/web/2008090513362/http://www.polonator.org/protocols/pet.aspx; Wayback Machine (Sep. 5, 2008) "PET (Paired End-Tag) Genomic Shotgun Library Construction Protocol".
Terry R, Porreca G, McCarthy K, Church GM. 2008. Polonator Instrument https://web.archive.org/web/20080905133855/http://www.polonator.org/protocols/pcr.aspx; Wayback Machine (Sep. 5, 2008) "Emulsion PCR Protocol".
Terry R, Porreca G, McCarthy K, Church GM. 2008. Polonator Instrument https://web.archive.org/web/20080905133913/http://www.polonator.org; Wayback Machine (Sep. 5, 2008) "Emulsion Breaking Protocol".
Terry R, Porreca G, McCarthy K, Church GM. 2008. Polonator Instrument https://web.archive.org/web/20080905133837/http://www.polonator.org/protocols/beadenrichment.aspx; Wayback Machine (Sep. 5, 2008) "Bead Enrichment Protocol".
Terry R, Porreca G, McCarthy K, Church GM. 2008. Polonator Instrument https://web.archive.org/web/20080905133372/http://www.polonator.org/protocols.beadcapping.aspx; Wayback Machine (Sep. 5, 2008) "Bead Capping Protocol".

(56) References Cited

OTHER PUBLICATIONS

Terry R, Porreca G, McCarthy K, Church GM. 2008. Polonator Instrument https://web.archive.org/web/20080905133372/http://www.polonator.org/protocols/coverslip.aspx; Wayback Machine (Sep. 5, 2008) "Coverslip Aminosilanation and Arraying Protocol".
Nov. 16, 2023—(US) Non-Final Office Action—U.S. Appl. No. 16/458,268.
Weibrecht, Irene et al., "Simultaneous Visualization of Both Signaling Cascade Activity and End-Point Gene Expression in Single Cells", PLOS ONE, vol. 6, No. 5, May 25, 2011 (May 25, 2011).
Larsson, Chatarina; Grundberg, Ida; Sbderberg, Ola; Nilsson, Mats: 11 In situ detection and genotyping of individual mRNA molecules, Nature Methods, vol. 7, No. 5 Apr. 11, 2010 (Apr. 11, 2010), pp. 395-397, XP055035168, DOI: 10.1038/nmeth.1448 Retrieved from the Internet: URL:http://www.nature.com/nmeth/journal/v7/n5/pdf/nmeth.1448.pdf [retrieved on Aug. 9, 2012] the whole document.
Nuovo: "Co-labeling Using In Situ PCR: A Review "Journal of Histochemistry & Cytochemistry, vol. 49, No. 11, Nov. 1, 2001 (Nov. 1, 2001), pp. 1329-1339, XP055164942, ISSN: 0022-1554, DOI: 10.1177/002215540104901101 the whole document.
Mitra R. D. et al: 11 In situ localized amplification and contact replication of many individual DNA molecules 11 Nucleic Acids Research, Information Retrieval LTD, GB, vol. 27, No. 24, Dec. 15, 1999 (Dec. 15, 1999), p. e34, XP002292358, ISSN: 0305-1048, DOI: 10.1093/NAR/27.24.E34 abstract.
Ke et al: 11 In situ sequencing for RNA analysis in preserved tissue and cells 11 Nature Methods, vol. 10, No. 9, Jul. 14, 2013 (Jul. 14, 2013), pp. 857-860, XP055163946, ISSN: 1548-7091, DOI: 10.1038/nmeth.2563 the whole document.
Lee et al: "Highly Multiplexed Subcellular RNA Sequencing in Situ", Science, vol. 343, No. 6177, Feb. 27, 2014 (Feb. 27, 2014), pp. 1360-1363, XP055305772, US ISSN: 0036-8075, DOI: 10.1126/science.1250212.
Clausson et al: "Compaction of rolling circle amplification products increases signal integrity and signal-to-noise ratio", Scientific Reports, vol. 5, Jul. 23, 2015 (Jul. 23, 2015), p. 12317, XP055305777, DOI: 10.1038/srep12317.
Nadji et al., "Photochemically and Photoenzymatically Cleavable DNA," J. Am. Chem. Soc. 1992, 114, 9266-9269.
Extended European Search Report and Written Opinion issued Dec. 17, 2019 for EP 19180827.8.
Supplementary European Search Report and Written Opinion issued Mar. 18, 2020.
Chen et al., "Expansion microscopy," Science, vol. 347, No. 6221, pp. 543-548 (Jan. 30, 2015).
Chozinski et al., "Expansion microscopy with conventional antibodies and fluorescent proteins," Nature Methods, vol. 13, No. 6, pp. 485-488 (Jun. 1, 2016).
Chen et al., "Nanoscale imaging of RNA with expansion microscopy," Nature Methods, vol. 133, No. 8, pp. 679-684 (Aug. 1, 2016).
Supplementary European Search Report issued Apr. 9, 2020 for EP 17847555.
Amasino, "Acceleration of nucleic acid hybridization rate by polyethylene glycol," Analytical Biochemistry, vol. 152, No. 2, pp. 304-307 (Feb. 1, 1986).
Bouché et al., "The effect of spermidine on endonuclease inhibition by agarose contaminants," Analytical Biochemistry, vol. 115, No. 1, pp. 42-45 (Jul. 15, 1981).
Kuznetsova et al., "What Macromolecular Crowding Can Do to a Protein," Int. J. Mol. Sci., vol. 15, No. 12, pp. 23090-23140 (Dec. 1, 2014).
Oupicky et al., "Laterally stabilized complexes of DNA with linear reducible polycations: Strategy for triggered intracellular actication of DNA delivery vectors," Journal of the American Chemical Society, vol. 124, No. 1, pp. 8-9 (Jan. 9, 2002).
Nguyen, Son C., "Strategies for Studying Chromatin Regulation and Organization," Doctoral Dissertation, Harvard University (May 1, 2018); retrieved from https://dash.harvard.edu/bitstream/handle/1/33493431/NGUYEN-DISSERTATION-2016.pdf?sequence=4&isAllowed=y on Apr. 8, 2020.

Zhou et al. "In Situ Detection of Messenger RNA Using Digoxigenin-Labeled Oligonucleotides and Rolling Circle Amplification" Experimental and Molecular Pathology 70, 281-288 (2001).
May 29, 2020—Examination Report issued for EP 18173059.9.
Jun. 1, 2020—Examination Report issued for GB 1809029.0.
Wright et al., "Dynamic closed-loop system for focus tracking using a spatial light modulator and a deformable membrane mirror," Optics Express, vol. 14, No. 1, pp. 222-228 (Jan. 9, 2006).
Wang et al., "The method of axial drift compensation of laser differential confocal microscopy based on zero-tracking," Proc. of SPIE, vol. 9618, 96180X (2015).
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Supplemental Material for Schweitzer et al. (PNAS 2000; 97(18):10113-10119) (Year: 2000).
Aug. 3, 2020—(US) Non-Final Office Action—U.S. Appl. No. 16/157,243.
Aug. 3, 2020 (US) Non-Final Office Action—U.S. Appl. No. 16/393,215.
Jul. 2, 2020—(US) Non-Final Office Action—U.S. Appl. No. 16/255,920.
Aug. 10, 2020—(GB) Examination Report—GB App. No. 1809029.0.
Sep. 24, 2020—(US) Final Office Action—U.S. Appl. No. 15/772,652.
Markaki et al. "Fluorescence In Situ Hybridization Applications for Super-Resolution 3D Structured Illumination Microscopy" Methods in Microbiology, Jan. 2013.
Achim et al. "High-throughput spatial mapping of single-cell RNA-seq data to tissue of origin" Nature Biotechnology, Apr. 13, 2015.
Sep. 25, 2020—(US) Non-Final Office Action—U.S. Appl. No. 16/386,337.
Aug. 25, 2020—(JP) Notice of Reasons for Rejection—App. No. 2018-522985.
PI: Piezo Nano Positioning, 2008 (online), retrieved on Aug. 12, 2020, pp. 1-6 <https://www.pi-USA.US/fileadmin/user_upload/pi_us/files/product_datasheets/N725_Piezo_Focus_Positioner.pdf>.
Sep. 14, 2020—(CA) Examination Report—App. No. 2,850,509.
Mali, P. et al. RNA-Guided Human Genome Engineering via Cas9. Science. Jan. 3, 2013, vol. 339; pp. 823-826; abstract; p. 823, second col. second to third paragraph; p. 823, third col. second paragraph to third paragraph; figure 1; Supplementary material, p. 4, first paragraph; p. 7, first paragraph; Supplementary figures S1, S3. DOI: 10.1126/science.1232033.
Tiley, LS et al. The VP16 Transcription Activation Domain is Functional When Targeted to A Promoter-Proximal RNA Sequence. Genes and Development. 1992. vol. 6; pp. 2077-2087; abstract; p. 2077, first col. first paragraph.
Trafton, A. Editing The Genome With High Precision [online]. MIT News office. Jan. 3, 2013 retrieved on Dec. 4, 2014). Retrieved from the Internet: <URL:http:/Inewsoffice.Trafton.edut2013/editing-the-genome-with-high-precision-0103 >; pp. 1-3; p. 3, third paragraph.
Leman, AR et al. The Replication Forie Understanding the Eukaryotic Replication Machinery and the Challenges to Genome Duplication. Genes. Jan. 29, 2013. vol. 4; pp. 1-32; figure 1; DOI: 10.3390/genes4010001.
Qi, L et al. Repurposing CRISPR as an RNA-Guided Platform For Sequence-Specific Control Of Gene Expression. Cell. Feb. 28, 2013. vol. 152; pp. 1173-1183; figures 2, 4. DOI: 10.1016/j.cell.2013.02.022.
Gasiunas, G et al Cas9-crRNA Ribonucleoprotein Complex Mediates Specific DNA Cleavage For Adaptive Immunity in Bacteria. PNAS. Sep. 4, 2012. vol. 109, No. 39; pp. E2579-E2586; p. E2583, first col. first paragraph. DOI: 10.1073/pnas.1208507109.
Cong, Let al. Multiplex Genome Engineering Using CRISPR/Cas Systems. Science. Jan. 3, 2013, vol. 339; pp. 819-823; abstract; p. 821, third column; p. 822, first col. first paragraph; figure 4. DOI: 10.1126/science.1231143.
Jinek, M et al. A Programmable Dual-RNA-Guided DNA Endonuclease in Adaptive Bacterial Immunity. Science. Jun. 28, 2012. vol. 337; pp. 816-821; DOI: 10.1126/science.1225829.

(56) References Cited

OTHER PUBLICATIONS

CRISPR In The Lab: A Practical Guide [online]. Addgene. Sep. 4, 2014. Retrieved on Dec. 4, 2014. Retrieved from the Internet: <URL: https://www.addgene.org/CRISPR/guide/>.
Cheng, AW et al. Multiplexed Activation of Endogenous Genes By CRISP R-on, an RNA-Guided Transcriptional Activator System. Cell Research. Aug. 27, 2013. vol. 23; pp. 1163-1171. DOI: 10.1038/cr.2013.122.
Mali, P. et al. CAS9 Transcriptional Activators for Target Specificity Screening and Paired Nickases for Cooperative Genome Engineering. Nature Biotechnology. Aug. 1, 2013. vol. 31; pp. 833-838; entire document. DOI: 10.1038/nbt.2675.
Ran, FA et al. Double Nicking By RNA-Guided CRISPR Cas9 for Enhanced Genome Editing Specificity. Cell. Sep. 12, 2013. vol. 154; pp. 1380-1389. DOI: 10.1016/j.cell.2013.08.021.
International Search Report and Written Opinion issued in corresponding International Application No. PCT/US14/40868, mailed Dec. 31, 2014.
Thisse et al. "High-Resolution in situ hybridization to whole-mount zebrafish embryos" 2008. Nature Protocols. vol. 3 No. 1 pp. 59-69. Doi:10.1038/nprot.2007.514.
Grompe (1993) Nature Genetics DOI: 10.1038/ng1093-111.
Office Action issued for corresponding European Patent Application No. 12780609.9, dated Sep. 23, 2015.
Seo, et al. Four-color DNA sequencing by synthesis on a chip using photocleavable fluorescent nucleotides. Proceeding of the National Academy of Sciences, Apr. 2005, 102 (17) 5926-5931.
Brenner, et al. "Gene expression analysis by massively parallel signature sequencing (MPSS) on microbead arrays". Nature Biotechnology vol. 18, pp. 630-634 (2000) doi:10.1038/76469.
Dec. 18, 2014 (PCT) International Preliminary Report—App PCT/US2013/044241.
Shendure Jay et al., "Accurate multiplex polony sequencing of an evolved bacterial genome," Science, American Association for the Advancement of Science, Washington, DC; US, vol. 309, No. 5741, Sep. 1, 2005, pp. 1728-1732, XP002427180, ISSN: 0036-8075, DOI: 10.1126/SCIENCE.1117839.
Extended European Seach Report issued in corresponding European Application No. 12860433.7, dated Aug. 13, 2015.
International Search Report and Written Opinion issued in corresponding International Application No. PCT/US2012/071398, mailed Apr. 8, 2013.
Benner et al. "Gene Expression analysis by massively parallel signature sequencing (MPSS) on microbead arrays". Nature Biotechnology, vol. 18, pp. 630-634 (Jun. 31, 2000).
Han et al. "Quantum-dot-tagged microbeads for multiplexed optical coding of biomolecules". Nature Biotechnology, vol. 19, 99. 631-635 (Jul. 31, 2001).
Lee, JH et al. Highly Multiplexed Subcellular RNA Sequencing In Situ. Science. Mar. 21, 2014, vol. 343, No. 6177; pp. 1360-1363; abstract; p. 1360, second col. second paragraph to third col. first paragraph; p. 1361, first col. first paragraph; p. 1363, first col. second paragraph to second col. first paragraph; DOI: 10.1126/science.1250212.
Ascano, M et al. Identification of RNA-Protein Interaction Networks Using PAR-CLIP. Wiley Interdiscip Rev RNA. Mar. 2012, vol. 3, No. 2; pp. 159-177; p. 3, third paragraph; p. 16, figure 1; p. 25, figure 6; DOI: 10.1002/wrna.1103.
Ginart, P et al. RNA Sequencing In Situ. Nat Biotechnol. Jun. 2014, vol. 32, No. 6; pp. 543-544; DOI: 10.1038/nbt.2921.
Saliba, AE et al. Single-Cell RNA-Seq: Advances And Future Challenges. Nucleic Acids Res. Jul. 22, 2014, vol. 42, No. 14; pp. 8845-8860; DOI: 10.1093/nar/gku555.
Eliscovich et al. mRNA on the move: The road to its biological destiny. Journal of Biological Chemistry, vol. 288, No. 28, pp. 20361-20368, Jul. 2013, in press May 2013 (Year: 2013).
Weis et al. Protein targeting to subcellular organelles via mRNA localization. Biochimica et Biophysica Acta, vol. 1833, pp. 260-273, 2013, available online Apr. 2012 (Year: 2012).
Jambhekar et al. Cis-acting determinants of asymmetric, cytoplasmic RNA transport. RNA, vol. 13, pp. 625-642, 2007 (Year: 2007).
Singer-Kruger et al. Here, there, everywhere. RNA Biology, vol. 11, No. 8, pp. 1031-1039, Aug. 2014. (Year: 2014).
Matlin et al. Spatial expression of the genome: the signal hypothesis at forty. Nature Reviews. Molecular Cell Biology, vol. 12, No. 5, pp. 333-340, May 2011, Epub Apr. 2011. (Year: 2011).
Polidoros et al. Rolling circle amplification-RACE: a method for simultaneous isolation of 5' and 3' cDNA ends from amplified cDNA templates. Bio Techniques, vol. 41, No. 1, pp. 35, 36, 38 and 40, Jul. 2006, including p. 1/1 of Supplementary Material. (Year: 2006).
Tsaftaris et al. Isolation of three homologous AP1-like MADS-box genes in crocus (*Crocus sativus* L.) and characterization of their expression. Plant Science, vol. 166, No. 5, pp. 1235-1243, May 2004. (Year: 2004).
Meeks et al. Characterization of genes encoding poly(A) polymerases in plants: Evidence for duplication and functional specialization. PLoS ONE, vol. 4, No. 11, e8082, Nov. 2009, printed as pp. 1/10-10/10. (Year: 2009).
Kalivas et al. famRCA-RACE: A rolling circle amplification RACE for isolating a family of homologous cDNAs in one reaction . . . Preparative Biochemistry and Biotechnology, vol. 40, No. 3, pp. 177-187, Jul. 2010. (Year: 2010).
Thisse et al. 2008 Nature protocols vol. 3 No. 1 pp. 59-69. Doi:10.1038/nprot.2007.514.
Doillon et al. "Actin Filaments in Normal Dermis and During Wound Healing" The American Journal of Pathology, vol. 126 Issue 1 (1987): pp. 164-170; p. 164 col. 1 para 1, p. 170 col. 1 para 2, fig. 4A-C.
International Search Report and Written Opinion based on PCT/US2018/027583 issued Jun. 29, 2018.
Soderberg, Ola et al., "Direct observation of individual endogenous protein complexes in situ by proximity ligation," Nature Methods, Dec. 2006, pp. 995-1000, vol. 3, No. 12, Nature Publishing Group.
Schweitzer, Barry et al., "Immunoassays with rolling circle DNA amplification: A versatile platform for ultrasensitive antigen detection" PNAS, Aug. 29, 2000, pp. 10113-10119, vol. 97, No. 18.
Cao, Yi et al., "In-situ immuno-PCR to detect antigens," The Lancet, Sep. 16, 2000, pp. 1002-1003, vol. 356.
Sano, Takeshi et al. "Immuno-PCR: Very Sensitive Antigen Detection by Means of Specific Antibody-DNA Conjugates," Science, Oct. 2, 1992, pp. 120-122, vol. 258.
Dasari, Vivek et al., "Platform for Spatial Molecular Data by Vivek Dasari 1-7 Sig nature redacted Thesis Supervisor", Aug. 20, 2015 (Aug. 20, 2015), XP055559164, Retreived from the Internet: URL:http://dspace.mit.edu/bitstream/handle/1721.1/107103/971494098-MIT.pdf?sequence=1 [retreived on Feb. 20, 2019].
Extended European Search Report issued May 13, 2019 for EP Application No. 16862929.3.
Lee, Je Hyuk et al., "Fluorescent in situ sequencing (FISSEQ) or RNA for gene expression profiling in intact cells and tissues", Nature Protocols, vol. 10, No. 3, Feb. 12, 2015 (Feb. 12, 2015), pp. 442-458. XP055272042, GB ISSN: 1754-2189, DOI: 10.1038/nprot.2014.191.
Extended European Search Report issued May 21, 2019 for European Application No. 16862945.9.
Choi, Harry M.T. et al., "Next-Generation in Situ Hybridization Chain Reaction: Higher Gain, Lower Cost, Greater Durability" ACS Nano, vol. 8, No. 5, May 27, 2014 (May 27, 2014), pp. 4284-4294, XP055409053, US.
Ravan, Hadi, et al. "Isothermal RNA detection through the formation of DNA concatemers contiaining HRP-mimicking DNAzymes on the surface of gold nanoparticles", Biosensors and Bioelectronics, Elsevier Science LTD. UK, Amsterdam, NL, vol. 80, Jan. 18, 2016 (Jan. 18, 2016), pp. 67-73, XP029441324.
Extended European Search Report issued for EP Application No. 17790240.0 on Sep. 4, 2019.
Brown et al., Review Article : In situ Hybridization with Riboprobes : An Overview for Veterinary Pathologists. Veterinary Pathology 35 : 159-167 (Year: 1998).

(56) References Cited

OTHER PUBLICATIONS

Choi et al., Programmable in situ amplification for multiplexed imaging of mRNA expression. Nature Biotechnology 28 (11): 1208 (Year: 2010).
Choi & Love et al., Immuno-Hybridization Chain Reaction for Enhancing Detection of Individual Cytokine-Secreting Human Peripheral Mononuclear Cells. Analytical Chemistry 83 : 6890-6895 (Year: 2011).
Hansen et al., Sensitive ligand-based protein quantification using immuno-PCR: A critical review of single-probe and proximity ligation assays. Biotechniques 56:217-228 (Year: 2014).
Kuimelis et al., Cleavage properties of an oligonucleotide containing a bridged internucleotide 5-phosphorothioate RNA linkage. Nucleic Acids Research 23 (23) : 4753-4760 (Year: 1999).
Mag et al., Synthesis and selective cleavage of an oligodeoxynucleotide containing a bridged internucleotide 5'-phosphorothioate linkage. Nucleic Acids Research 19(7): 1437 (Year: 1991).
Richardson et al., Experimental and Theoretical Studies of Light-to-Heat Conversion and Collective Heating Effects in Metal Nanoparticle Solutions. Nano Letters 9(3) : 1139-1146 (Year: 2009).
Song et al., Hybridization chain reaction-based aptameric system for the highly selective and sensitive detection of protein. Analyst 137: 1396 (Year: 2012).
Xiao et al., Single-step electronic detection of femtomolar DNA by target-induced strand displacement in an electrode-bound duplex. PNAS 103(45): 16677-16680 (Year: 2006).
Zhang et al., Dynamic DNA nanotechnology using strand-displacement reactions. Nature Chemistry 3 : 103-113 (Year: 2011).
Zhao et al., An electrochemical aptasensor based on hybridization chain reaction with enzyme-signal amplification for interferon-gamma detection. Biosensors and Bioelectronics 36: 129-134 (Year: 2012).
Srinivas et al., On the biophysics and kinetics of toehold-mediated DNA strand displacement. Nucleic Acids Research 41 (22) : 10641-10658 (Year: 2013).
Terry R, Porreca G, McCarthy K, Church GM. 2008. Polonator Instrument https://web.archive.org/web/20080905133800/http://www.polonator.org; Wayback Machine (Sep. 5, 2008) "Polony Sequence by Ligation Protocol".
Terry R, Porreca G, McCarthy K, Church GM. 2008. Polonator Instrument https://web.archive.org/web/20080705172604/http://www.polonator.org; Wayback Machine (Jul. 5, 2008) "Polony Sequence Protocols".
Terry R, Porreca G, McCarthy K, Church GM. 2008. Polonator Instrument https://web.archive.org/web/20080905133818/http://www.polonator.org; Wayback Machine (Sep. 5, 2008) "Help Wanted".
Terry R, Porreca G, McCarthy K, Church GM. 2008. Polonator Instrument https://web.archive.org/web/20080807155529/http://www.polonator.org/software.aspx; Wayback Machine (Aug. 7, 2008) "Software".
Terry R, Porreca G, McCarthy K, Church GM. 2008. Polonator Instrument https://web.archive.org/web/20080807155404/http://www.polonator.org; Wayback Machine (Aug. 7, 2008) "Reagent Kits".
Terry R, Porreca G, McCarthy K, Church GM. 2008. Polonator Instrument https://web.archive.org/web/20080905133541/http://www.polonator.org/reagentkits/run.aspx; Wayback Machine (Sep. 5, 2008) "Run Kits".
Terry R, Porreca G, McCarthy K, Church GM. 2008. Polonator Instrument https://web.archive.org/web/20080905133601/http://www.polonator.org/reagentkits.pairedtag.aspx; Wayback Machine (Sep. 5, 2008) "Paired-Leg Library Kits".
Terry R, Porreca G, McCarthy K, Church GM. 2008. Polonator Instrument https://web.archive.org/web/20080905133741/http://www.polonator.org/reagentkits.emulsion.aspx; Wayback Machine (Sep. 5, 2008) "Emulsion PCR/Bead Capping Kits".
Terry R, Porreca G, McCarthy K, Church GM. 2008. Polonator Instrument https://web.archive.org/web/20080905133702/http://www.polonator.org/reagentkits/enrichment.aspx; Wayback Machine (Sep. 5, 2008) "Enrichment Kits".
Terry R, Porreca G, McCarthy K, Church GM. 2008. Polonator Instrument https://web.archive.org/web/20080807155316/http://www.polonator.org/flowcells.aspx; Wayback Machine (Aug. 7, 2008) "Flow Cells".
Church GM. 2006. "Genomes for all" Sci Am 294: 46-54.
De Bakker PI, Yelensky R, Pe'er I, Gabriel SB, Daly MJ, Altshuler D. 2005. "Efficiency and power in genetic association studies" Nat Genet 37: 1217-23.
Dixon AL, Liang L, Moffatt MF, Chen W, Heath S, Wong KC, Taylor J, Burnett E, Gut I, Farrall M, Lathrop GM, Abecasis GR, Cookson WO. 2007. "A genome-wide association study of global gene expression" Nat Genet 39: 1202-7.
Emilsson V, Thorleifsson G, Zhang B, Leonardson AS, Zink F, Zhu J, Carlson S, Helgason A, Walters GB, Gunnarsdottir S, Mouy M, Steinthorsdottir V, Eiriksdottir GH, Bjornsdottir G, Reynisdottir I, Gudbjartsson D, Helgadottir A, Jonasdottir A, Jonasdottir A, Styrkarsdottir U, Gretarsdottir S, Magnusson KP, Stefansson H, Fossdal R, Kristjansson K, Gislason HG, Stefansson T, Leifsson BG, Thorsteinsdottir U, Lamb JR, Gulcher JR, Reitman ML, Kong A, Schadt EE, Stefansson K. 2008; "Genetics of gene expression and its effect on disease" Nature 452: 423-8.
Risch N, Merikangas K. 1996. "The future of genetic studies of complex human diseases" Science 273: 1516-7.
Schadt EE, Monks SA, Drake TA, Lusis AJ, Che N, Colinayo V, Ruff TG, Milligan SB, Lamb JR, Cavet G, Linsley PS, Mao M, Stoughton RB, Friend SH. 2003. "Genetics of gene expression surveyed in maize, mouse and man" Nature 422: 297-302.
Altshuler D, Daly MJ, Lander ES. 2008. "Genetic mapping in human disease" Science 322: 881-8.
Cookson W, Liang L, Abecasis G, Moffatt M, Lathrop M. 2009. "Mapping complex disease traits with global gene expression" Nat Rev Genet 10: 184-94.
International HapMap C. 2005. "A haplotype map of the human genome" Nature 437: 1299-320. PMC ID: PMC1880871.
Klein RJ. 2007. "Power analysis for genome-wide association studies" BMC Genet 8: 58. PMC ID: PMC2042984.
Kwan T, Benovoy D, Dias C, Gurd S, Provencher C, Beaulieu P, Hudson TJ, Sladek R, Majewski J. 2008. "Genome-wide analysis of transcript isoform variation in humans" Nat Genet 40: 225-31.
McCarroll SA. 2008. "Extending genome-wide association studies to copy-number variation" Hum Mol Genet 17: R135-42.
Morley M, Molony CM, Weber TM, Devlin JL, Ewens KG, Spielman RS, Cheung VG. 2004. "Genetic analysis of genome-wide variation in human gene expression" Nature 430: 743-7.
Sachidanandam R, Weissman D, Schmidt SC, Kakol JM, Stein LD, Marth G, Sherry S, Mullikin JC, Mortimore BJ, Willey DL, Hunt SE, Cole CG, Coggill PC, Rice CM, Ning Z, Rogers J, Bentley DR, Kwok PY, Mardis ER, Yeh RT, Schultz B, Cook L, Davenport R, Dante M, Fulton L, Hillier L, Waterston RH, McPherson JD, Gilman B, Schaffner S, Van Etten WJ, Reich D, Higgins J, Daly MJ, Blumenstiel B, Baldwin J, Stange-Thomann N, Zody MC, Linton L, Lander ES, Altshuler D, International SNPMWG. 2001. A map of human genome sequence variation containing 1.42 million.
Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. "Mapping the genetic architecture of gene expression in human liver" PLoS Biol 6: e107. PMC ID: PMC2365981.
Serre D, Gurd S, Ge B, Sladek R, Sinnett D, Harmsen E, Bibikova M, Chudin E, Barker DL, Dickinson T, Fan JB, Hudson TJ. 2008. "Differential allelic expression in the human genome: a robust approach to identify genetic and epigenetic cis-acting mechanisms regulating gene expression" PLoS Genet 4: e1000006. PMC ID: PMC2265535.
Ball MP, Li JB, Gao Y, Lee J, LeProust E, Park I-H, Xie B, Daley GQ, Church GM. 2009. "Targeted and whole-genome methylomics reveals gene-body signatures in human cell lines" Nat Biotechnol 27: 361-8.
Brenner S, Williams SR, Vermaas EH, Storck T, Moon K, McCollum C, Mao JI, Luo S, Kirchner JJ, Eletr S, DuBridge RB, Burcham

(56) References Cited

OTHER PUBLICATIONS

T, Albrecht G. 2000. "In vitro cloning of complex mixtures of DNA on microbeads: physical separation of differentially expressed cDNAs" Proc Natl Acad Sci U S A 97: 1665-70. PMC ID: PMC26493.
Chiang DY, Getz G, Jaffe DB, O'Kelly MJ, Zhao X, Carter SL, Russ C, Nusbaum C, Meyerson M, Lander ES. 2009. "High-resolution mapping of copy-number alterations with massively parallel sequencing" Nat Methods 6: 99-103. PMC ID: PMC2630795.
Choy E, Yelensky R, Bonakdar S, Plenge RM, Saxena R, De Jager PL, Shaw SY, Wolfish CS, Slavik JM, Cotsapas C, Rivas M, Dermitzakis ET, Cahir-McFarland E, Kieff E, Hafler D, Daly MJ, Altshuler D. 2008. "Genetic analysis of human traits in vitro: drug response and gene expression in lymphoblastoid cell lines" PLoS Genet 4: e1000287. PMC ID: PMC2583954.
Christian AT, Pattee MS, Attix CM, Reed BE, Sorensen KJ, Tucker JD. 2001. "Detection of DNA point mutations and mRNA expression levels by rolling circle amplification in individual cells" Proc Natl Acad Sci U S A 98: 14238-43. PMC ID: PMC64666.
Church GM, Porreca GJ, Terry RC, Lares M. 2008. "High-Speed Imaging for DNA Sequencing" Biophotonics (<http://www.photonics.com/Content/ReadArticle.aspx?ArticleID=33989>).
Deng J, Shoemaker R, Xie B, Gore A, LeProust EM, Antosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylation associated with nuclear reprogramming" Nat Biotechnol 27: 353-60.
Eberwine J, Kacharmina JE, Andrews C, Miyashiro K, McIntosh T, Becker K, Barrett T, Hinkle D, Dent G, Marciano P. 2001. "mRna expression analysis of tissue sections and single cells" J Neurosci 21: 8310-4.
Kolb HC, Finn Mg, B. Sk. 2001. "Click Chemistry: Diverse Chemical Function from a Few Good Reactions" Angew. Chem. Int. 40: 2004-21.
Kwiatkowski M, Fredriksson S, Isaksson A, Nilsson M, Landegren U. 1999. "Inversion of in situ synthesized oligonucleotides: improved reagents for hybridization and primer extension in DNA microarrays" Nucleic Acids Res 27: 4710-4. PMC ID: PMC148770.
Li JB, Gao Y, Aach J, Zhang K, Kryukov GV, Xie B, Ahlford A, Yoon J-K, Rosenbaum AM, Wait-Zaranek A, LeProust E, Sunyaev S, Church GM. 2009. "Multiplex padlock capture and sequencing reveal human hypermutable CpG variations" Genome Res in press.
Mitra RD, Butty VL, Shendure J, Williams BR, Housman DE, Church GM. 2003. "Digital genotyping and haplotyping with polymerase colonies" Proc Natl Acad Sci U S A 100: 5926-31. PMC ID: PMC156303.
Pan X, Urban AE, Palejev D, Schulz V, Grubert F, Hu Y, Snyder M, Weissman SM. 2008. "A procedure for highly specific, sensitive, and unbiased whole-genome amplification" Proc Natl Acad Sci U S A 105: 15499-504. PMC ID: PMC2563063.
Stougaard M, Lohmann JS, Zajac M, Hamilton-Dutoit S, Koch J. 2007. "In situ detection of non-polyadenylated RNA molecules using Turtle Probes and target primed rolling circle Prins" BMC Biotechnol 7: 69. PMC ID: PMC2203993.
Wang Z, Gerstein M, Snyder M. 2009. "RNA-Seq: a revolutionary tool for transcriptomics" Nat Rev Genet 10: 57-63.
Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci U S A 104: 16462-7. PMC ID: PMC2034218.
Zhang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" (submitted to Nature Methods).
Bakal C, Aach J, Church G, Perrimon N. 2007. "Quantitative morphological signatures define local signaling networks regulating cell morphology" Science 316: 1753-6.
Bang D, Church GM. 2008. "Gene synthesis by circular assembly amplification" Nat Methods 5: 37-9.
Bell J. 2004. "Predicting disease using genomics" Nature 429: 453-6.
Eid J, Fehr A, Gray J, Luong K, Lyle J, Otto G, Peluso P, Rank D, Baybayan P, Bettman B, Bibillo A, Bjornson K, Chaudhuri B, Christians F, Cicero R, Clark S, Dalal R, Dewinter A, Dixon J, Foquet M, Gaertner A, Hardenbol P, Heiner C, Hester K, Holden D, Kearns G, Kong X, Kuse R, Lacroix Y, Lin S, Lundquist P, Ma C, Marks P, Maxham M, Murphy D, Park I, Pham T, Phillips M, Roy J, Sebra R, Shen G, Sorenson J, Tomaney A, Travers K, Trulson M, Vieceli J, Wegener J, Wu D, Yang A, Zaccarin D, Zhao P, Zhong F, Korlach J, Turner S. 2009. Real-time DNA sequencing.
Harris TD, Buzby PR, Babcock H, Beer E, Bowers J, Braslavsky I, Causey M, Colonell J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320: 106-9.
Kim JB, Porreca GJ, Song L, Greenway SC, Gorham JM, Church GM, Seidman CE, Seidman JG. 2007. "Polony multiplex analysis of gene expression (PMAGE) in mouse hypertrophic cardiomyopathy" Science 316: 1481-4.
Kurimoto K, Yabuta Y, Ohinata Y, Saitou M. 2007. "Global single-cell cDNA amplification to provide a template for representative high-density oligonucleotide microarray analysis" Nat Protoc 2: 739-52.
Drmanac et al. "Human Genome Sequencing Using Unchained Base Reads on Self-Assembling DNA Nanoarrays" Science; vol. 327; pp. 78-81; Jan. 1, 2010.
Islam et al. "Characterization of the single-cell transcriptional landscape by highly multiplex RNA-seq" Genome Research; vol. 21; May 4, 2011; pp. 1160-1167.
Larsson et al. "In situ detection and genotyping of individual mRNA molecules" Nature Methods; vol. 7; No. 5; May 2010; pp. 395-397.
Larsson et al. "In situ genotyping individual DNA molecules by target-primed rolling-circle amplification of padlock probes" Nature Methods; vol. 1; No. 3; Dec. 2004; pp. 227-232.
Shendure et al. "Accurate Multiplex Polony Sequence of an Evolved Bacterial Genome" Science; vol. 309; Sep. 9, 2005; pp. 1728-1732.
Zenklusen, Daniel and SINGER, Robert H. "Analyzing mRNA Expression Using Single mRNA Resolution Fluorescent in Situ Hybridization" Methods in Enzymology, vol. 470, <https://www.ncbi.nlm.nih.gov/pmc/articles/PMC3162037/>, pp. 1-17, Mar. 1, 2010.
Zenklusen, Daniel and Singer, Robert H. "Analyzing mRNA Expression Using Single mRNA Resolution Fluorescent in Situ Hybridization" Methods in Enzymology, 2010, vol. 470, pp. 641-659.
Stougaard et al. "In situ detection of non-polyadenylated RNA molecules using Turtle Probes and target primed rolling circle Prins" BMC Biotechnology; 7:69; Oct. 18, 2007; pp. 1-10.

\* cited by examiner

No shear stress  
DNA amplicons (0.5–2 um diameter)

5 min high shear stress  
No cross-linking  
Stretched out DNA amplicons (20–100 um diameter)

5 min high shear stress  
Aminoallyl dUTP cross-linking  
Morphologically preserved DNA amplicons DNA amplicons crosslinked in fibroblasts July 2011 | March 2012

Probe | Strip | Probe

METHOD OF SELECTIVELY SEQUENCING AMPLICONS IN A BIOLOGICAL SAMPLE

RELATED APPLICATION DATA

This application is a continuation application of U.S. patent application Ser. No. 17/708,050, filed on Mar. 30, 2022, which is a continuation application of U.S. patent application Ser. No. 17/363,097, now U.S. Pat. No. 11,299,767, filed on Jun. 30, 2021, which is a continuation application of U.S. patent application Ser. No. 16/157,243, now U.S. Pat. No. 11,078,520, filed on Oct. 11, 2018, which is a continuation application of U.S. patent application Ser. No. 14/774,282, now U.S. Pat. No. 10,138,509, filed on Sep. 10, 2015, which is a National Stage Application under 35 U.S.C. 371 of PCT Application No. PCT/US2014/018580 designating the United States and filed Feb. 26, 2014; which claims the benefit of U.S. Provisional Application No. 61/777,383 and filed Mar. 12, 2013 each of which are hereby incorporated by reference in their entireties.

STATEMENT OF GOVERNMENT INTERESTS

This invention was made with government support under HL102815, and HG005550 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on Aug. 29, 2024, is named "Sequence_Listing_010498_01587_ST26" and is 3.56 KB in size.

FIELD OF THE INVENTION

The present invention relates to methods of making a three-dimensional matrix of nucleic acids and amplifying, detecting and sequencing such nucleic acids within the matrix.

BACKGROUND OF THE INVENTION

Since many gene products such as RNA and proteins are enriched in regions where they function, their location provides an important clue to their function. This property has been used for in situ fluorescent hybridization, immunohistochemistry and tissue-specific reporter assays in numerous areas of biological research.

Current methods involve extracting nucleic acid molecules from their native environment or making synthetic nucleic acid molecules, amplifying them in solution and placing them on a flat array surface or beads for gene detecting via hybridization or sequencing, making it impossible to identify the cellular origin of individual nucleic acids.

SUMMARY

Embodiments of the present invention are directed to methods of making a three dimensional matrix of nucleic acids. Embodiments of the present invention are directed to methods of making a three dimensional matrix including nucleic acids covalently bound into a matrix or into or to a matrix material. The nucleic acids may be co-polymerized with the matrix material or cross-linked to the matrix material or both. According to one aspect, a plurality of nucleic acid sequences of certain length, such as DNA or RNA sequences are part of a three-dimensional copolymer. The nucleic acids may then be amplified and sequenced in situ, i.e. within the matrix. The three-dimensional matrix of nucleic acids provides, in a certain aspect, an information storage medium where the nucleic acids, i.e. a sequence of one or more nucleotides, represent stored information which can be read within the three-dimensional matrix. According to one aspect, nucleic acids such as DNA or RNA sequences of given length are covalently attached to a matrix material to preserve their spatial orientation in the x, y and z axes within the matrix. It is to be understood that the three dimensional matrix may include a matrix material and that the term copolymer, matrix and matrix material may be used interchangeably.

According to one aspect, methods described herein are directed to immobilizing naturally occurring nucleic acids within their native environment, such as within a cell or within a tissue sample. The three dimensional nucleic acid matrix can be generated in situ in a cell or tissue sample to preserve the naturally occurring nucleic acid sequence diversity (such as DNA and RNA) and spatial orientation in cells, tissues or any other complex biomaterial. According to this aspect, the location of nucleic acids and their relative position is identified as a three dimensional structure, such as within subcellular compartments, within cells, within tissues, as three dimensional nucleic acid assemblies, as three dimensional nucleic acid material, etc. The nucleic acids can be amplified and sequenced, if desired, in situ thereby providing positional information of the nucleic acids within the cell or tissue.

According to a related aspect, nucleic acids of interest, whether naturally occurring or synthetic, can be present within a three dimensional matrix material and covalently attached to the three dimensional matrix material such that the relative position of each nucleic acid is fixed, i.e. immobilized, within the three dimensional matrix material. In this manner, a three-dimensional matrix of covalently bound nucleic acids of any desired sequence is provided. Each nucleic acid has its own three dimensional coordinates within the matrix material and each nucleic acid represents information. In this manner, a large amount of information can be stored in a three dimensional matrix. Individual information-encoding nucleic acids, such as DNA or RNA can be amplified and sequenced in situ, i.e., within the matrix, thereby enabling a large amount of information to be stored and read in a suitable three dimensional material.

According to a further aspect, the nucleic acids can be amplified to produce amplicons within the three dimensional matrix material. The amplicons can then be covalently attached to the matrix, for example, by copolymerization or cross-linking. This results in a structurally stable and chemically stable three dimensional matrix of nucleic acids. According to this aspect, the three dimensional matrix of nucleic acids allows for prolonged information storage and read-out cycles. The nucleic acid/amplicon matrix allows for high throughput sequencing of a wide ranging array of biological and non-biological samples in three dimensions.

According to certain aspects, a three dimensional nucleic acid matrix is provided where a plurality of nucleic acid molecules, such as DNA or RNA, amplicons or nucleic acid structural units are immobilized, such as by covalent bonding to the matrix, in a three dimensional space relative to one another. In this context, the nucleic acid molecules are rigidly fixed to the extent that they maintain their coordinate position within the matrix. It is to be understood that even though a nucleic acid molecule may be covalently attached to the three dimensional matrix material, the nucleic acid molecule itself may be capable of movement though bound to the matrix, such as for example, when a nucleic acid sequence is bound to the matrix at a single location on the nucleic acid.

According to one aspect, the three dimensional matrix including nucleic acids is porous. According to one aspect, the three dimensional matrix including nucleic acids is porous to the extent that reagents typically used in amplification methods can diffuse or otherwise move through the matrix to contact nucleic acids and thereby amplify nucleic acids under suitable conditions.

According to one aspect, the three dimensional matrix material is chemically inert and thermally stable to allow for various reaction conditions and reaction temperatures. According to this aspect, the three dimensional matrix material is chemically inert and thermally stable to conditions used in amplification and sequencing methods known to those of skill in the art.

According to one aspect, the three dimensional matrix material is optically transparent. According to one aspect, the three dimensional matrix material is optically transparent to allow for three dimensional imaging techniques known to those of skill in the art.

According to one aspect, the nucleic acids are amplified to an extent to produce sufficient levels of amplicons for three dimensional imaging. For example, the nucleic acids are amplified and include a label sufficient for a high level of fluorescence compatible with three dimensional imaging.

According to one aspect, the material used to form the matrix is compatible with a wide range of biological and non-biological specimens in situ so as to avoid extracting the nucleic acid molecules away from their native environment.

According to one aspect, the matrix material may be a semi-solid medium that can be made from polyacrylamide, cellulose, alginate, polyamide, cross-linked agarose, cross-linked dextran or cross-linked polyethylene glycol. In certain aspects, the semi-solid medium has x, y and z axes, and the nucleic acids are present randomly or non-randomly within the three dimensional matrix.

According to one aspect, the matrix material is porous. Porosity can result from polymerization and/or crosslinking of molecules used to make the matrix material. The diffusion property within the gel matrix is largely a function of the pore size. The molecular sieve size is chosen to allow for rapid diffusion of enzymes, oligonucleotides, formamide and other buffers used for amplification and sequencing (>50-nm). The molecular sieve size is also chosen so that large DNA or RNA amplicons do not readily diffuse within the matrix (<500-nm). The porosity is controlled by changing the cross-linking density, the chain lengths and the percentage of co-polymerized branching monomers according to methods known to those of skill in the art.

In certain aspects, the semi-solid medium can be attached to a solid support such as a microscope slide or a flow cell. The solid support can be attached to the bottom surface of the semi-solid medium.

BRIEF DESCRIPTION OF THE DRAWINGS

The foregoing and other features and advantages of the present invention will be more fully understood from the following detailed description of illustrative embodiments taken in conjunction with the accompanying drawings.

DETAILED DESCRIPTION

Figure 1:
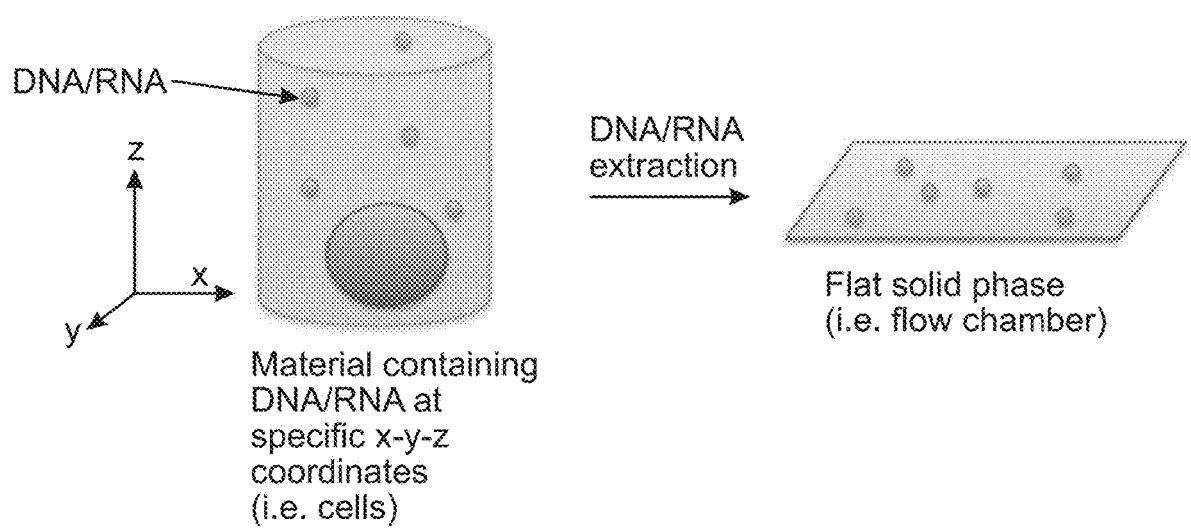
FIG. 1 depicts a schematic of nucleic acids at relative positions within a three dimension environment and extraction and placement onto a two dimensional environment, such as a glass slide or flow chamber.

The present invention provides a three dimensional matrix of a plurality of nucleic acids. The present invention provides a three dimensional matrix including a plurality of nucleic acids bound thereto. According to one aspect, the matrix is a three dimensional nucleic acid-containing polymer. The nucleic acids may be naturally occurring nucleic acids or non-naturally occurring nucleic acids, such as nucleic acids that have been made using synthetic methods. The nucleic acids in the three dimensional matrix may be ordered or unordered. The nucleic acids in the three dimensional matrix may be present in their natural spatial relationship within a cell, tissue or organism. The nucleic acids in the three dimensional matrix may be present in rows and columns within the three dimensional matrix.

According to one aspect, the nucleic acids are modified to incorporate a functional moiety for attachment to the matrix. The functional moiety can be covalently cross-linked, copolymerize with or otherwise non-covalently bound to the matrix. The functional moiety can react with a cross-linker. The functional moiety can be part of a ligand-ligand binding pair. dNTP or dUTP can be modified with the functional group, so that the function moiety is introduced into the DNA during amplification. A suitable exemplary functional moiety includes an amine, acrydite, alkyne, biotin, azide, and thiol. In the case of crosslinking, the functional moiety is cross-linked to modified dNTP or dUTP or both. Suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix. Suitable exemplary spacer moieties include polyethylene glycol, carbon spacers, photo-cleavable spacers and other spacers known to those of skill in the art and the like.

According to one aspect, a matrix-forming material is contacted to a plurality of nucleic acids spatially arrange in three-dimensions relative to one another.

Matrix forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art.

According to one aspect, a matrix-forming material can be introduced into a cell. The cells are fixed with formaldehyde and then immersed in ethanol to disrupt the lipid membrane. The matrix forming reagents are added to the sample and are allowed to permeate throughout the cell. A polymerization inducing catalyst, UV or functional cross-linkers are then added to allow the formation of a gel matrix. The un-incorporated material is washed out and any remaining functionally reactive group is quenched. Exemplary cells include any cell, human or otherwise, including diseased cells or healthy cells. Certain cells include human cells, non-human cells, human stem cells, mouse stem cells, primary cell lines, immortalized cell lines, primary and immortalized fibroblasts, HeLa cells and neurons.

According to one aspect, a matrix-forming material can be used to encapsulate a biological sample, such as a tissue sample. The formalin-fixed embedded tissues on glass slides are incubated with xylene and washed using ethanol to remove the embedding wax. They are then treated with Proteinase K to permeabilized the tissue. A polymerization inducing catalyst, UV or functional cross-linkers are then added to allow the formation of a gel matrix. The un-incorporated material is washed out and any remaining functionally reactive group is quenched. Exemplary tissue samples include any tissue samples of interest whether human or non-human. Such tissue samples include those from skin tissue, muscle tissue, bone tissue, organ tissue and the like. Exemplary tissues include human and mouse brain tissue sections, embryo sections, tissue array sections, and whole insect and worm embryos.

The matrix-forming material forms a three dimensional matrix including the plurality of nucleic acids. According to one aspect, the matrix-forming material forms a three dimensional matrix including the plurality of nucleic acids while maintaining the spatial relationship of the nucleic acids. In this aspect, the plurality of nucleic acids are immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise cross-linking with the matrix-forming material. The plurality of nucleic acids may also be immobilized within the matrix by covalent attachment or through ligand-protein interaction to the matrix.

According to one aspect, the matrix is porous thereby allowing the introduction of reagents into the matrix at the site of a nucleic acid for amplification of the nucleic acid. A porous matrix may be made according to methods known to those of skill in the art. In one example, a polyacrylamide gel matrix is co-polymerized with acrydite-modified streptavidin monomers and biotinylated DNA molecules, using a suitable acrylamide:bis-acrylamide ratio to control the cross-linking density. Additional control over the molecular sieve size and density is achieved by adding additional cross-linkers such as functionalized polyethylene glycols. According to one aspect, the nucleic acids, which may represent individual bits of information, are readily accessed by oligonucleotides, such as labeled oligonucleotide probes, primers, enzymes and other reagents with rapid kinetics.

According to one aspect, the matrix is sufficiently optically transparent or otherwise has optical properties suitable for standard Next Generation sequencing chemistries and deep three dimensional imaging for high throughput information readout. The Next Generation sequencing chemistries that utilize fluorescence imaging include ABI SoLiD (Life Technologies), in which a sequencing primer on a template is ligated to a library of fluorescently labeled nonamers with a cleavable terminator. After ligation, the beads are then imaged using four color channels (FITC, Cy3, Texas Red and Cy5). The terminator is then cleaved off leaving a free-end to engage in the next ligation-extension cycle. After all dinucleotide combinations have been determined, the images are mapped to the color code space to determine the specific base calls per template. The workflow is achieved using an automated fluidics and imaging device (i.e. SoLiD 5500 W Genome Analyzer, ABI Life Technologies). Another sequencing platform uses sequencing by synthesis, in which a pool of single nucleotide with a cleavable terminator is incorporated using DNA polymerase. After imaging, the terminator is cleaved and the cycle is repeated. The fluorescence images are then analyzed to call bases for each DNA amplicons within the flow cell (HiSeq, Illumia).

According to certain aspects, the plurality of nucleic acids may be amplified to produce amplicons by methods known to those of skill in the art. The amplicons may be immobilized within the matrix generally at the location of the nucleic acid being amplified, thereby creating a localized colony of amplicons. The amplicons may be immobilized within the matrix by steric factors. The amplicons may also be immobilized within the matrix by covalent or noncovalent bonding. In this manner, the amplicons may be considered to be attached to the matrix. By being immobilized to the matrix, such as by covalent bonding or crosslinking, the size and spatial relationship of the original amplicons is maintained. By being immobilized to the matrix, such as by covalent bonding or crosslinking, the amplicons are resistant to movement or unraveling under mechanical stress.

According to one aspect, the amplicons, such as DNA amplicons, are then copolymerized and/or covalently attached to the surrounding matrix thereby preserving their spatial relationship and any information inherent thereto. For example, if the amplicons are those generated from DNA or RNA within a cell embedded in the matrix, the amplicons can also be functionalized to form covalent attachment to the matrix preserving their spatial information within the cell thereby providing a subcellular localization distribution pattern.

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in Molecular Biology of the Cell, 3d edition, Garland Publishing, 1994, incorporated herein by reference in its entirety for all purposes.

As used herein, the term "nucleic acid" includes the term "oligonucleotide" or "polynucleotide" which includes a plurality of nucleotides. The term "nucleic acid" is intended to include naturally occurring nucleic acids and synthetic nucleic acids. The term "nucleic acid" is intended to include single stranded nucleic acids and double stranded nucleic acids. The term "nucleic acid" is intended to include DNA and RNA, whether single stranded or double stranded. Nucleotides of the present invention will typically be the naturally-occurring nucleotides such as nucleotides derived from adenosine, guanosine, uridine, cytidine and thymidine. When oligonucleotides are referred to as "double-stranded," it is understood by those of skill in the art that a pair of oligonucleotides exists in a hydrogen-bonded, helical array typically associated with, for example, DNA. In addition to the 100% complementary form of double-stranded oligonucleotides, the term "double-stranded" as used herein is also meant to include those form which include such structural features as bulges and loops (see Stryer, Biochemistry, Third Ed. (1988), incorporated herein by reference in its entirety for all purposes). As used herein, the term "polynucleotide" refers to a strand of nucleic acids that can be a variety of different sizes. Polynucleotides may be the same size as an oligonucleotide, or may be two-times, three-times, four-times, five-times, ten-times, or greater than the size of an oligonucleotide.

Oligonucleotides and/or polynucleotides may be isolated from natural sources or purchased from commercial sources. Oligonucleotide and/or polynucleotide sequences may be prepared by any suitable method, e.g., the phosphoramidite method described by Beaucage and Carruthers ((1981) Tetrahedron Lett. 22:1859) or the triester method according to Matteucci et al. (1981) J. Am. Chem. Soc. 103:3185), both incorporated herein by reference in their entirety for all purposes, or by other chemical methods using either a commercial automated oligonucleotide synthesizer or high-throughput, high-density array methods described herein and known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain embodiments of the invention oligonucleotides and/or polynucleotides may be prepared using a variety of microarray technologies known in the art. Pre-synthesized oligonucleotide and/or polynucleotide sequences may be attached to a support or synthesized in situ using light-directed methods, flow channel and spotting methods, inkjet methods, pin-based methods and bead-based methods set forth in the following references: McGall et al. (1996) Proc. Natl. Acad. Sci. U.S.A. 93:13555; Synthetic DNA Arrays In Genetic Engineering, Vol. 20:111, Plenum Press (1998); Duggan et al. (1999) Nat. Genet. S21: 10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Application Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; incorporated herein by reference in their entirety for all purposes.

Nucleic acids may be obtained from libraries, e.g., genomic libraries, cDNA libraries and the like. Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233, incorporated herein by reference in their entirety for all purposes.

In certain embodiments, nucleic acids are those found naturally in a biological sample, such as a cell or tissue.

In still other aspects, a matrix is used in conjunction with a solid support. For example the matrix can be polymerized in such a way that one surface of the matrix is attached to a solid support (e.g., a glass surface), while the other surface of the matrix is exposed or sandwiched between two solid supports. According to one aspect, the matrix can be contained within a container.

Solid supports of the invention may be fashioned into a variety of shapes. In certain embodiments, the solid support is substantially planar. Examples of solid supports include plates such as slides, microtitre plates, flow cells, coverslips, microchips, and the like, containers such as microfuge tubes, test tubes and the like, tubing, sheets, pads, films and the like. Additionally, the solid supports may be, for example, biological, nonbiological, organic, inorganic, or a combination thereof.

Embodiments of the present invention are further directed to the amplification of nucleic acid sequences within the matrix, i.e. in situ, within the matrix. Methods of amplifying nucleic acids include rolling circle amplification in situ. In certain aspects, methods of amplifying nucleic acids involves the use of PCR, such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. U.S.A. 91:360-364; incorporated herein by reference in their entirety for all purposes). Alternative amplification methods include: self sustained sequence replication (Guatelli et al. (1990) Proc. Natl. Acad. Sci. USA 87:1874, incorporated herein by reference in its entirety for all purposes), transcriptional amplification system (Kwoh et al. (1989) Proc. Natl. Acad. Sci. US. 86:1173, incorporated herein by reference in its entirety for all purposes), Q-Beta Replicase (Lizardi et al. (1988) BioTechnology 6:1197, incorporated herein by reference in its entirety for all purposes), recursive PCR (Jaffe et al. (2000) J. Biol. Chem. 275:2619; and Williams et al. (2002) J. Biol. Chem. 277:7790; incorporated herein by reference in their entirety for all purposes) or any other nucleic acid amplification method using techniques well known to those of skill in the art. A variety of amplification methods are described in U.S. Pat. Nos. 6,391,544, 6,365,375, 6,294,323, 6,261,797, 6,124,090 and 5,612,199, incorporated herein by reference in their entirety for all purposes.

Embodiments of the present invention are directed to methods of amplifying nucleic acids in situ within the matrix by contacting the nucleic acids within the matrix with reagents and under suitable reaction conditions sufficient to amplify the nucleic acids. According to one aspect, the matrix is porous to allow migration of reagents into the matrix to contact the nucleic acids. In certain aspects, oligonucleotides are amplified by selectively hybridizing an amplification primer to an amplification site at the 3' end of an oligonucleotide using conventional methods. Amplification primers are 6 to 100, and even up to 1,000, nucleotides in length, but typically from 10 to 40 nucleotides, although oligonucleotides of different length are of use. Amplification primers may be present in solution to be added to the matrix or they may be added during formation of the matrix to be present therein sufficiently adjacent to nucleic acids to allow for hybridization and amplification.

Typically, selective hybridization occurs when two nucleic acid sequences are substantially complementary, i.e., at least about 65% 75%, 80%, 85%, 90%, 91%, 92%, 93%, 94%, 95%, 96%, 97%, 98% 99%, 99.1%, 99.2%, 99.3%, 99.4%, 99.5%, 99.6%, 99.7%, 99.8%, 99.9% or 100% complementary over a stretch of at least 14 to 25 nucleotides. See Kanchisa, M., 1984, Nucleic Acids Res. 12:203, incorporated herein by reference in its entirety for all purposes.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher Tm than do shorter ones, and are less likely to be repeated within a given target sequence, thereby cutting down on promiscuous hybridization. Primer sequences with a high G-C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G-C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g., formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about 1M, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone. Hybridization conditions are known to those skilled in the art and can be found in Current Protocols in Molecular Biology, John Wiley & Sons, N.Y. (1989), 6.3.1-6.3.6, incorporated herein by reference in its entirety for all purposes.

Primers are designed with the above first four considerations in mind. While estimates of the relative merits of numerous sequences are made mentally, computer programs have been designed to assist in the evaluation of these several parameters and the optimization of primer sequences (see, e.g., Hoover et al. (2002) Nucleic Acids Res. 30: e43, and Rouillard et al. (2004) Nucleic Acids Res. 32: W176, incorporated by reference herein in their entirety for all purposes).

In accordance with certain examples, methods of sequencing nucleic acid in situ within a matrix are provided. General sequencing methods known in the art, such as sequencing by extension with reversible terminators, fluorescent in situ sequencing (FISSEQ), pyrosequencing, massively parallel signature sequencing (MPSS) and the like (described in Shendure et al. (2004) Nat. Rev. 5:335, incorporated herein by reference in its entirety), are suitable for use with the matrix in which the nucleic acids are present. Reversible termination methods use step-wise sequencing-by-synthesis biochemistry that coupled with reversible termination and removable fluorescence (Shendure et al. supra ands U.S. Pat. Nos. 5,750,341 and 6,306,597, incorporated herein by reference. FISSEQ is a method whereby DNA is extended by adding a single type of fluorescently-labelled nucleotide triphosphate to the reaction, washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described further in Mitra et al. (2003) Anal. Biochem. 320:55, incorporated herein by reference in its entirety for all purposes. Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) Science 281:363, incorporated herein by reference in its entirety for all purposes. MPSS utilizes ligation-based DNA sequencing simultaneously on microbeads. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) Nat. Biotech. 18:630, incorporated herein by reference in its entirety for all purposes.

According to certain aspects, the nucleic acids within the matrix can be interrogated using methods known to those of skill in the art including fluorescently labeled oligonucleotide/DNA/RNA hybridization, primer extension with labeled ddNTP, sequencing by ligation and sequencing by synthesis. Ligated circular padlock probes described in Larsson, et al., (2004), Nat. Methods 1:227-232 can be used to detect multiple sequence targets in parallel, followed by either sequencing-by-ligation, -synthesis or -hybridization of the barcode sequences in the padlock probe to identify individual targets.

According to one aspect, methods described herein produce a three dimensional nucleic acid amplicon matrix which is stable, long-lasting and resistant, substantially resistant or partially resistant to enzymatic or chemical degradation. The three dimensional nucleic acid amplicon matrix can be repeatedly interrogated using standard probe hybridization and/or fluorescence based sequencing. The three dimensional nucleic acid amplicon matrix can be repeatedly interrogated with little or no signal degradation, such as after more than 50 cycles, and with little position shift, such as less than 1 µm per amplicon.

According to one aspect, a plurality of circular DNA molecules are covalently linked to one another. The circular DNA molecules are then amplified using methods known to those of skill in the art, such as isothermal enzymatic amplification one example of which is rolling circle amplification. According to this aspect, the amplicons are localized near the circular DNA. According to this aspect, the amplicons form a shell around the circular DNA or otherwise assemble around the circular DNA. Each circular DNA may have more than 1000 amplicons surrounding or otherwise associated therewith. According to this aspect, the amplicons surrounding a particular circular DNA provide a high signal intensity, due in part to the number of amplicons and/or detectable labels associated with the amplicons. The amplicons may be functionalized and cross-linked or otherwise covalently bound together around their associate circular DNA to form a series or network of tightly bound DNA amplicon shells around each circular DNA. The series or network of tightly bound DNA amplicon shells around each circular DNA may be assembled onto a three-dimensional support. According to one aspect, the series or network of tightly bound DNA amplicon shells around each circular DNA may be assembled onto a three-dimensional support producing a three dimensional DNA polymer with defined overall shape, size and amplicon position.

According to one aspect, amplicons are covalently linked without the need for separate cross-linkers, such as bis-N-succinimidyl-(nonaethylene glycol) ester. An acrydite moiety, such as a catalyst activated acrydite moiety is introduced at the end of a long carbon spacer (i.e., about C6 to about C12) at position 5 of a uracil base a representative formula of which is shown below.

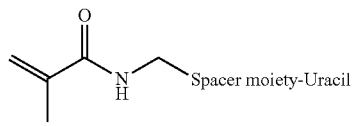

In the formula below, R represents the acrydite spacer moiety attached to the 5 position of the uracil base.

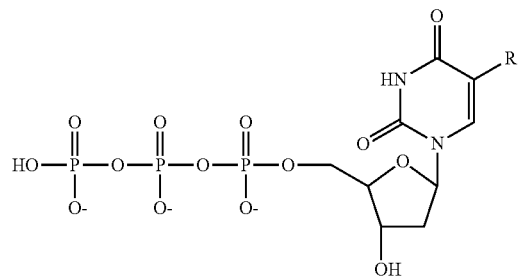

When copolymerized with bis-acrylamide in the presence of a catalyst, a polymerization reaction takes place, encapsulating the circular DNA with the amplicons and fixing the amplicons in position. The chemically inert nature of the polymerized mixture allows various downstream applications. The spacer can be a carbon chain of between about 2 carbons to about 200 carbons. The spacer can be polyethylene glycol. The length of the spacer can vary from about 30 angstroms to about 100 angstroms and can be of various molecular weights. The spacer can be permanent or reversible, such as by using UV light, enzymes, chemical cleavage, etc. A three dimensional matrix, such as a polyacrylamide gel matrix, can be used to embed a variety of biological structures containing enzymatically or chemically modified DNA or RNA molecules containing an acrydite functional moiety or moieties. The non-nucleic acid component is selectively dissolved using detergents, proteases, organic solvents or denaturants to create a three dimensional matrix that preserves individual DNA or RNA molecules and their relative spatial location. Examples include embedding cells, healthy and diseased tissues and tissue sections, small model organisms such as worms and insects, bacterial colonies or biofilm, environmental samples containing other DNA or RNA containing materials or organisms.

This invention is further illustrated by the following examples, which should not be construed as limiting. The contents of all references, patents and published patent applications cited throughout this application are hereby incorporated by reference in their entirety for all purposes.

Example I

Immobilizing, Amplifying and Imaging DNA/RNA Molecules within Cells

Human iPS cells or human primary fibroblasts are grown on a 1.5 cover slip. They are fixed using 4% formaldehyde in PBS for 15 min, followed by three washes of 70% ethanol. The reverse transcription mixture containing 1 uM random hexamer or 0.1 uM polydT(18) V primer (SEQ ID NO: 2) with additional adapter sequences (TCTCGG-GAACGCTGAAGA) (SEQ ID NO:1), 250 uM dNTP, 40 uM aminoallyl dUTP (Anaspec), 20U RNase inhibitor and 100 U MMuLV reverse transcriptase (Enzymatics) are then added to the fixed cells and incubated overnight at 37° C. The sample is then washed using PBS, and cross-linked using 100 uM BS (PEG) 9 (Thermo-Fisher Scientific) in PBS for 1 hour, followed by 1M Tris treatment for 15 min. The circularization mixture containing 25U CircLigase (Epicentre), 1 mM MnCl and 1 M Betain is added, and the sample is incubated at 60° C. for 2 hours. The residual RNA is degraded using a mixture of RNase cocktail (Roche) and RNase H (Enzymatics) at 37° C. for 1 hour. The RCA primer is then hybridized to the sample at 60° C. for 15 min and washed. For rolling circle amplification, 100 U phi29 DNA polymerase (Enzymatics), 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. For the DNA amplicon detection, 1 uM fluorescently label oligonucleotides are diluted in 2×SSC and hybridized to the matrix containing the DNA amplicons at 60° C. and washed. Imaging is done using Leica SP5 scanning confocal microscope using 10×, 20× or 63× objectives in four color channels (FITC, Cy3, Texas Red and Cy5). The image stacks containing up to 50 optical sections are then visualized using Imaris Bitplane software for three dimensional reconstruction of the DNA amplicons within the sample matrix.

Figure 2:
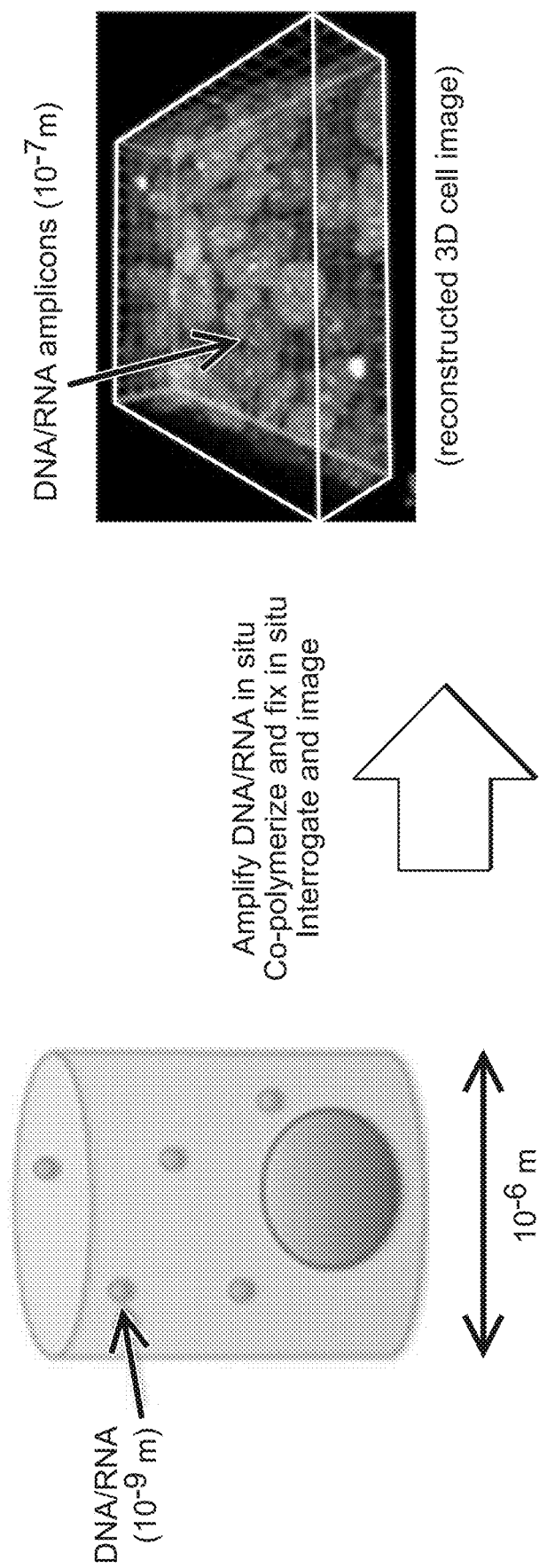
FIG. 2 depicts in schematic the process of creating a matrix of nucleic acids within cells in situ, followed by amplifying the nucleic acids, such as DNA or RNA, in situ, co-polymerizing the amplicons in situ, covalently attaching the amplicons to the matrix material, interrogating the amplicons and imaging the amplicons along with a reconstructed 3D cell image with DNA/RNA amplicons on the order of 10-7 m.

Methods described herein allow one to immobilize, amplify and image single DNA/RNA molecules in a three dimensional space without perturbing the structure. As shown in FIG. 2, single cells were grown in tissue culture. DNA/RNA was amplified in situ. The DNA/RNA was co-polymerized into a matrix material in situ, and individual amplicons were interrogated/hybridized with fluorescent oligonucleotides and imaged. When viewed under much higher magnification, individual amplicons can be imaged using confocal microscopy. This allows one to find out where different DNA/RNA molecules reside, how they are compartmentalized among different cell types and morphologies and how their representation changes over time in developing tissues. The similar concept can be used for many other specimens in both natural and synthetic materials, as long as they can be co-polymerized and/or encapsulated by the DNA amplicons.

According to one specific aspect, inside individual mammalian cells, 20 to 500K mRNA molecules are distributed throughput the cytoplasm (Islam et al., 2011). According to embodiment, cells are fixed and permeabilized. Cellular RNA is then converted into cDNA molecules using dUTP in place or in addition to dTTP. The cDNA molecules containing modified dUMP residues are then cross-linked to each other and circularized, forming a three dimensional pseudo-polymer of circular cDNA molecules inside individual cells. Then rolling circle amplification is used to amplify the cDNA network into a DNA amplicon network. This cell-based DNA amplicon network then stores information about each transcript's identity, location, variation/mutations, etc. The cell-based DNA amplicon matrix can be read using sequencing by ligation (i.e. ABI SoLiD), sequencing by synthesis (i.e. Illumina), or any other proprietary or open sequencing chemistries (see Drmanac et al., 2010; Shendure et al., 2005 herein incorporated by reference in their entireties). Given the three dimensional nature of the DNA amplicon network, one can use confocal or multi-photon microscopy to sequencing individual amplicons throughout the whole thickness of the amplicon network, enabling one to visualize the cDNA distribution of transcripts between the apical side and the basal side of the cells as shown in FIG. 2. Given the tight packing density, one can selectively read different subpopulations sequentially, reducing the density of information read at any given time and extending over time for better spatial resolution.

Example II

Immobilizing, Amplifying and Imaging DNA/RNA Molecules within a Fly Embryo

Drosophila embryos are fixed using 4% formaldehyde in PBS, followed by multiple washes of 70% ethanol. The embryos are then mounted on a cover glass using an optically transparent adhesive. The reverse transcription mixture containing 1 uM random hexamer or 0.1 uM polydT (18) V primer with additional adapter sequences (TCTCGG-GAACGCTGAAGA), 250 UM dNTP, 40 uM aminoallyl dUTP (Anaspec), 20U RNase inhibitor and 100 U MMuLV reverse transcriptase (Enzymatics) are then added to the fixed cells and incubated overnight at 37° C. The sample is then washed using PBS, and cross-linked using 100 uM BS (PEG) 9 (Thermo-Fisher Scientific) in PBS for 1 hour, followed by 1M Tris treatment for 15 min. The circularization mixture containing 25U CircLigase (Epicentre), 1 mM MnCl and 1 M Betain is added, and the sample is incubated at 60° C. for 2 hours. The residual RNA is degraded using a mixture of RNase cocktail (Roche) and RNase H (Enzymatics) at 37° C. for 1 hour. The RCA primer is then hybridized to the sample at 60° C. for 15 min and washed. For rolling circle amplification, 100 U phi29 DNA polymerase (Enzymatics), 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. For the DNA amplicon detection, 1 uM fluorescently label oligonucleotides are diluted in 2×SSC and hybridized to the matrix containing the DNA amplicons at 60° C. and washed. Imaging is done using Leica SP5 scanning confocal microscope using 10×, 20× or 63× objectives in four color channels (FITC, Cy3, Texas Red and Cy5). The image stacks are then visualized using Imaris Bitplane software for three dimensional reconstruction of the DNA amplicons within the sample matrix.

As shown in FIG. 2, fly embryos were obtained and DNA/RNA was amplified in situ. The DNA/RNA was copolymerized into a matrix material in situ, and individual amplicons were interrogated/hybridized with fluorescent oligonucleotides and imaged. When viewed under much higher magnification, individual amplicons can be imaged using confocal microscopy even in these thick biological specimens. This allows one to find out where different DNA/RNA molecules reside, how they are compartmentalized among different cell types and morphologies and how their representation changes over time in developing tissues. The similar concept can be used for many other specimens in both natural and synthetic materials, as long as they can be co-polymerized and/or encapsulated by the DNA amplicons.

Example III

Immobilizing, Amplifying and Imaging DNA/RNA Molecules within Mouse Brain

A fresh frozen adult mouse brain sections (20-um cryo-sections) are fixed using 4% formaldehyde in PBS. It is then treated with 0.4 ug/ml Proteinase K for 30 min at room temperature and thoroughly washed using 70%, 95% and 100% ethanol. The reverse transcription mixture containing 1 uM random hexamer or 0.1 uM polydT (18) V primer with additional adapter sequences (TCTCGGGAACGCTGAAGA), 250 uM dNTP, 40 uM aminoallyl dUTP (Anaspec), 20U RNase inhibitor and 100 U MMuLV reverse transcriptase (Enzymatics) are then added to the fixed cells and incubated overnight at 37° C. The sample is then washed using PBS, and cross-linked using 100 uM BS (PEG) 9 (Thermo-Fisher Scientific) in PBS for 1 hour, followed by 1M Tris treatment for 15 min. The circularization mixture containing 25U CircLigase (Epicentre), 1 mM MnCl and 1 M Betain is added, and the sample is incubated at 60° C. for 2 hours. The residual RNA is degraded using a mixture of RNase cocktail (Roche) and RNase H (Enzymatics) at 37° C. for 1 hour. The RCA primer is then hybridized to the sample at 60° C. for 15 min and washed. For rolling circle amplification, 100 U phi29 DNA polymerase (Enzymatics), 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. For the DNA amplicon detection, 1 uM fluorescently label oligonucleotides are diluted in 2×SSC and hybridized to the matrix containing the DNA amplicons at 60° C. and washed. Imaging is done using Leica epifluorescence microscope using a 10× objective in four color channels (FITC, Cy3, Texas Red and Cy5) in a tiled scan mode (20 by 15 separate images). The images are then stitched together during the image acquisition and visualized using Imaris Bitplane software.

As shown in FIG. 2, mouse brain sections were obtained and DNA/RNA was amplified in situ. The DNA/RNA was copolymerized into a matrix material in situ, and individual amplicons were interrogated/hybridized with fluorescent oligonucleotides and imaged. When viewed under much higher magnification, individual amplicons can be imaged using confocal microscopy even in these thick biological specimens. This allows one to find out where different DNA/RNA molecules reside, how they are compartmentalized among different cell types and morphologies and how their representation changes over time in developing tissues. The similar concept can be used for many other specimens in both natural and synthetic materials, as long as they can be co-polymerized and/or encapsulated by the DNA amplicons.

Example IV

Crosslinking of Amplicons

A 50-base oligonucleotide is phosphorylated at the 5' end using polynucleotide kinase in the T4 ligase buffer for 15 min. The reaction mixture is incubated with CircLigase mixture at 60° C. for 1 hour to generate circular templates for testing. The RCA primer (18 bases) is then hybridized to the circular template in solution and a diluted template:primer mixture is used for rolling circle amplification. The RCA reaction solution contained 0, 0.1 uM, 1 uM or 10 uM aminoallyl dUTP in addition to the normal dNTP. The reaction mixture was then loaded onto an 1% agarose gel and visualized using SYBR safe dyes.

Figure 3:
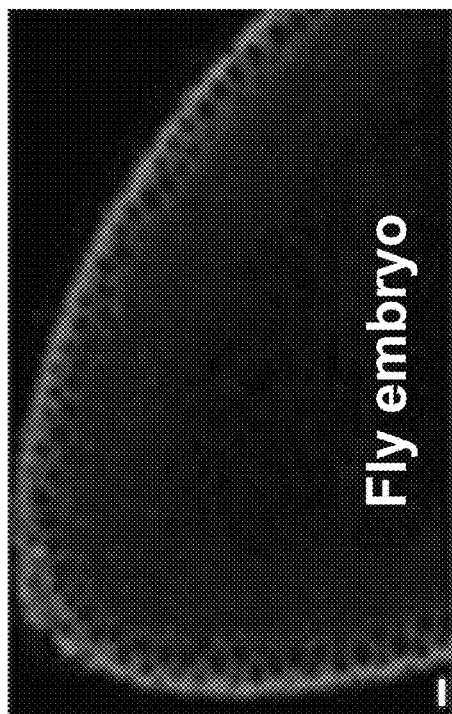
FIG. 3 is an image of a whole mount *Drosophila* embryo.

The incorporation of aminoallyl dUTP that is later cross-linked to each other and to the amine exposing substrate still allows for reverse transcription using M-MuLV reverse transcriptase and rolling circle amplification using Phi29 DNA polymerase, albeit at a reduced rate in a concentration dependent manner. Increasing amounts of aminoallyl dUTP were added as a competitor to dTTP present in the amplification mixture in solution. The rolling circle amplicons are single stranded DNA which are highly folded. As shown in FIG. 3A, these structures run as a single large band around ~ 10-15-kb on an 1% agarose gel.

Example V

The Incorporation of Aminoallyl dUTP Leads to Slightly Smaller Diameter of the Average DNA Amplicon Size A 50-base oligonucleotide is phosphorylated at the 5' end using polynucleotide kinase in the T4 ligase buffer for 15 min. The reaction mixture is incubated with CircLigase mixture at 60° C. for 1 hour to generate circular templates for testing. The RCA primer (18 bases) is then hybridized to the circular template in solution and a diluted template:primer mixture is used for rolling circle amplification. The RCA reaction solution contained aminoallyl dUTP and normal dNTP at varying ratios (1:50 to 1:50,000). After 8 hours of RCA, the reaction mixture was diluted in PBS and bound to amino-silane treated coverglass. The bound RCA amplicons were then visualized by staining it with SYBR safe and imaging it using an epifluorescence microscope (63× objective). The images were then processed using Imaris Bitplane to identify individual amplicons and measure the average diameter of each spot.

The incorporation of aminoallyl dUTP leads to slightly smaller diameter of the average DNA amplicon size. The circular cDNA template was used for rolling circle amplification, during which a range of aminoallyl dUTP was added. The amplicon mixture in solution was then arrayed on a glass surface and hybridized to a common fluorescent probe sequence. Since aminoallyl dUTP has a single positive charge, the increasing incorporation of aminoallyl dUTP led to a reduction in the overall negative charge, making each DNA amplicon slightly more compact. As shown in FIG. 3B, the ratio shown in the graph legend represents the molar ratio of aminoallyl dUTP to dTTP during the amplification step.

Example VI

Aminoallyl dUTP Cross-Linking Preserves DNA Amplicons

A 50-base oligonucleotide is phosphorylated at the 5' end using polynucleotide kinase in the T4 ligase buffer for 15 min. The reaction mixture is incubated with CircLigase mixture at 60° C. for 1 hour to generate circular templates for testing. The RCA primer (18 bases) is then hybridized to the circular template in solution and a diluted template:primer mixture is used for rolling circle amplification with or without aminoallyl dUTP. After 8 hours of RCA, the reaction mixture was diluted in PBS and bound to amino-silane treated coverglass. The bound RCA amplicons were then cross-linked with BS (PEG) 9. They were then washed using a continuous stream of 2×SSC wash solution for 1 min, stained with SYBR safe and imaged using an epifluorescence microscope (63× objective).

The DNA amplicons generated in solution are arrayed on a glass surface and cross-linked via the aminoallyl moiety. They were then exposed to a constant flow of distilled water running across its surface with and with the cross-linker chemistry for 5 min at room temperature and then imaged after SYBR Gold staining. As shown in FIG. 3C, the DNA amplicons that were not cross-linked stretched out as a result of high shear stress for about 5 minutes. The DNA amplicons cross-linked with aminoallyl dUTP were morphologically preserved after high shear stress for 5 minutes.

Example VII

DNA Amplicons in Human Fibroblasts are Structurally and Chemically Stable

Human primary fibroblasts are grown on a 1.5 cover slip. They are fixed using 4% formaldehyde in PBS for 15 min, followed by three washes of 70% ethanol. The reverse transcription mixture containing 1 uM random hexamer or 0.1 uM polydT (18) V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS (PEG) 9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed. Imaging is done using Leica SP5 scanning confocal microscope using a 63× objectives. The fluorescent oligonucleotides are stripped off using 80% formamide heated to 80° C. The sample is then dried and stored at 4° C. from July 2011 to March 2012. The sample was rehydrated in PBS, and rehybridized to the fluorescently labeled oligonucleotides and imaged. The second image was obtained using an epifluorescence microscope.

Figure 4:
FIG. 4 is an optical section of a fly embryo.

The DNA amplicons are structurally and chemically stable over a long period of time once cross-linked. As shown in FIG. 4A, the DNA amplicons preserved as a three dimensional matrix in human fibroblasts can be interrogated using fluorescent primers and stored in phosphate buffered solution for up to a year and re-interrogated without losing their structural or sequence information. The different image quality here reflects the difference between confocal microscopy vs. epifluorescence microscopy, not the sample quality.

Example VIII

A DNA Amplicon Matrix within a Cell is Structurally and Chemically Stable

Human primary fibroblasts are grown on a 1.5 cover slip. They are fixed using 4% formaldehyde in PBS for 15 min, followed by three washes of 70% ethanol. The reverse transcription mixture containing 1 uM random hexamer or 0.1 uM polydT (18) V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS (PEG) 9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed. Imaging is done using Leica SP5 scanning confocal microscope using a 63× objectives. The fluorescent oligonucleotides are stripped off using 80% formamide heated to 80° C. The sample is then washed with distilled water and rehybridized to the fluorescently labeled oligonucleotides and imaged.

As shown in FIG. 4B, the DNA amplicon matrix inside the cell can be stripped using harsh chemical agents (i.e. 0.1N NaOH, 80% formamide) and heated up to 95° C. for a prolonged period of time without losing their structural integrity or definition.

Example IX

A DNA Amplicon Matrix within a Cell is Structurally and Chemically Stable

Human iPS cells are grown on a 1.5 cover slip. They are fixed using 4% formaldehyde in PBS for 15 min, followed by three washes of 70% ethanol. The reverse transcription mixture containing 1 uM random hexamer or 0.1 uM polydT (18) V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS (PEG) 9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed three times using 2×SSC. After imaging, the fluorescent oligonucleotides are stripped off using 80% formamide heated to 80° C. The sample is then washed with distilled water and rehybridized to the fluorescently labeled oligonucleotides. This cycle is repeated sixty times (5 minutes per cycle). The multiple images were then aligned and processed using MatLab to identify a region of interest. Up to twenty single cells and amplicons within the cells were chosen and compared to the cell-free region for determining the signal to noise ratio after each hybridization and stripping cycle. The sample was then used for 12 cycles of sequencing by ligation. After sequencing, the 12 image stacks (19 optical sections per field) were analyzed on Imaris Bitplane and individual DNA amplicons were tracked over the whole sequencing run. Only those amplicons that were identified in all 12 cycles were analyzed.

As shown in FIG. 4C, the sample can be cycled through more than 50 heating, cooling, enzymatic and chemical reactions without any changes in the signal to noise ratio. The high absolute signal intensity here was due to insufficient probe washing in the initial cycles. When the individual DNA amplicons in the matrix was imaged in three dimensions using confocal microscopy and tracked over 12 cycles, one measure the relative displacement of each amplicon over time. Despite numerous thermal, chemical and enzymatic manipulations, the mean displacement of each amplicon was ~500-nm in both lateral and axial dimensions, which was about the diameter of each amplicon. An example image of the analysis is shown in the right panel, in which the line representing the displacement is shown in different colors according to their cycle number.

Example X

DNA Amplicons Embedded within a Cross-Linked Matrix in a Cell are Imaged

Human iPS cells are grown on a 1.5 cover slip. They are fixed using 4% formaldehyde in PBS for 15 min, followed by three washes of 70% ethanol. The reverse transcription mixture containing 1 uM random hexamer or 0.1 uM polydT (18) V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS (PEG) 9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. For the DNA amplicon detection, 1 uM fluorescently labeled oligonucleotides are diluted in 2×SSC and hybridized to the matrix containing the DNA amplicons at 60° C. and washed three times using 2×SSC. Leica SP5 scanning confocal microscope with 63× objective is used and scanning optical zoom of 5× is used. The line scan was repeated three times and averaged to generate a high quality image.

Figure 5:
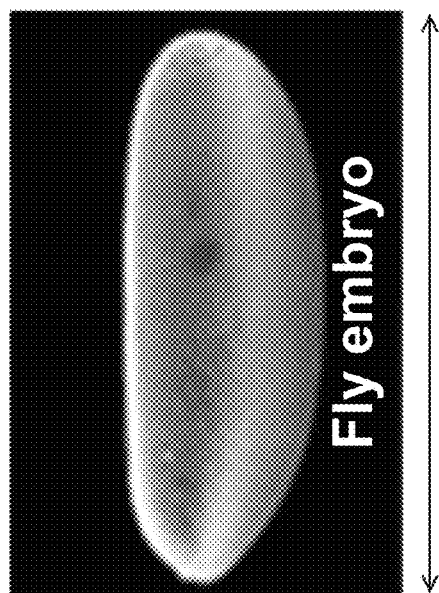
FIG. 5 is an image of a whole mount mouse brain section.

FIG. 5A is an image of the DNA amplicons (derived from reverse transcription of the cytoplasmic and the nuclear RNA) embedded within the cross-linked matrix inside human induced pluripotent stem cells. Individual amplicons are too tightly packed to visualize discrete amplicons, given the optical diffraction limitation in microscopy. But various subcellular compartments where the RNA is not expected to be present (i.e. nm: nuclear membrane, pm: plasma membrane) show dark staining, whereas the nucleus (Nu) and the cytoplasm (Cy) show a high density of the amplicons. The distribution of the cellular RNA show unique patterns from cell to cell (1st panel vs. 2nd panel) and from one cell cycle phase to another (1st panel vs. 3rd panel). These results show that the DNA amplicons can be immobilized, amplified and interrogated in a manner to reflect their original spatial information.

Example XI

DNA Amplicons Embedded within a Cross-Linked Matrix in a Cell are Sequenced

Human iPS cells are grown on a 1.5 cover slip. They are fixed using 4% formaldehyde in PBS for 15 min, followed by three washes of 70% ethanol. The reverse transcription mixture containing 1 uM random hexamer or 0.1 uM polydT (18) V primer with additional adapter sequences, 250 uM dNTP, 40 uM aminoallyl dUTP, 20U RNase inhibitor and 100 U M-MuLV reverse transcriptase are then added to the fixed cells and incubated overnight at 37° C. The sample is then washed using PBS, and cross-linked using 100 uM BS (PEG) 9 in PBS for 1 hour, followed by 1M Tris treatment for 15 min. The circularization mixture containing 25 U CircLigase, 1 mM MnCl and 1 M Betain is added, and the sample is incubated at 60° C. The residual RNA is degraded using a mixture of RNase cocktail and RNase H. The RCA primer is then hybridized to the sample at 60° C. for 15 min. For rolling circle amplification, 100 U phi29 DNA polymerase, 250 uM dNTP and 40 uM aminoallyl dNTP are added to the sample and incubated at 30° C. overnight. The sample is then washed using PBS, and cross-linked using 100 uM BS (PEG) 9 in PBS for 1 hour, followed by 1M Tris treatment for 15 min. The sequencing primer is designed with different 3' ends that that each primer can detect only ¼th of the amplicons. If different dinucleotides are added to the 3' ends of the primer, each primer can detect only ¹⁄₁₆th of the amplicons. A chosen sequencing primer in 2×SSC is hybridized to the sample at 60° C. for 15 minutes and washed. A ligation mixture containing 10 U T4 DNA ligase, ligation buffer and 1 uM fluorescently labeled nonamers (a pool containing A, G, C or T at fixed positions and labeled with FITC, Cy3, Texas Red or Cy5, respectively) is added and incubated for 50 min at room temperature. After washing three times with 2×SSC, the cell is imaged on Leica SP5 scanning confocal microscope using four color channels. After imaging, the probe complex is stripped using 80% formamide and washed with distilled water. The sequencing by ligation step is repeated using a different nonamer set interrogating the next sequence.

Using selective sequencing primers, only a subset of the total amplicons can be sequenced for better spatial resolution. The left panel shows a subset of randomly primed cDNA amplicons being sequenced on a confocal microscope. The right panel shows GAPDH cDNA amplicons being sequenced over time using confocal microscopy. Only a single optical section is shown here. The axial dimension represents time or sequencing cycle steps.

Example XII

Circular DNA is Cross-Linked or Co-Polymerized into a Matrix and Amplified

Figure 6:
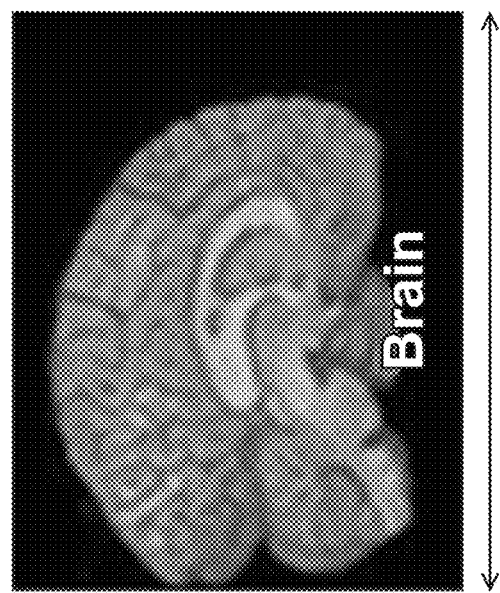
FIG. 6 is an optical section of a mouse brain.
Figure 7A:
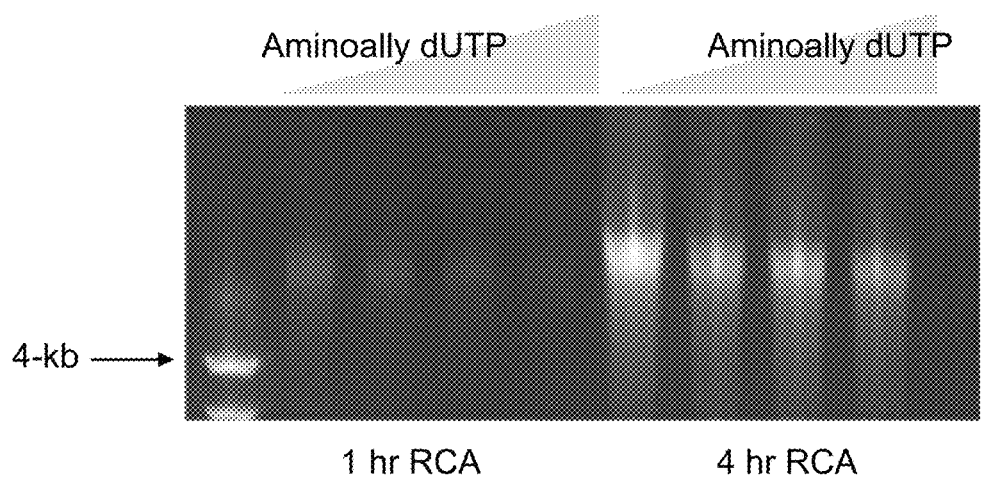
FIG. 7A is a gel image of aminoallyl dUTP after 1 hour of rolling circle amplification and after 4 hours of rolling circle amplification
Figure 7B:
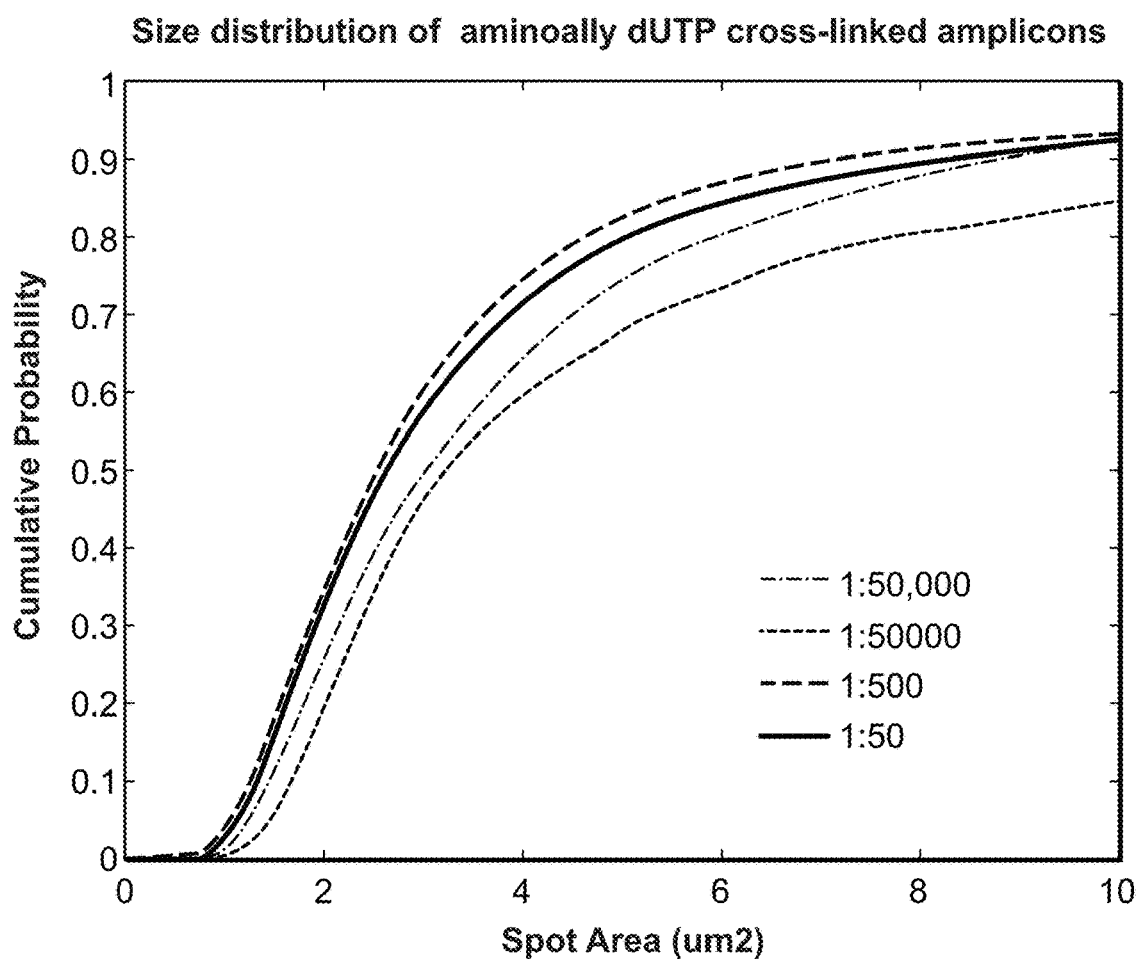
FIG. 7B is a graph representative of the molar ratio of aminoallyl dUTP to dTTP during amplification.
Figure 7C:
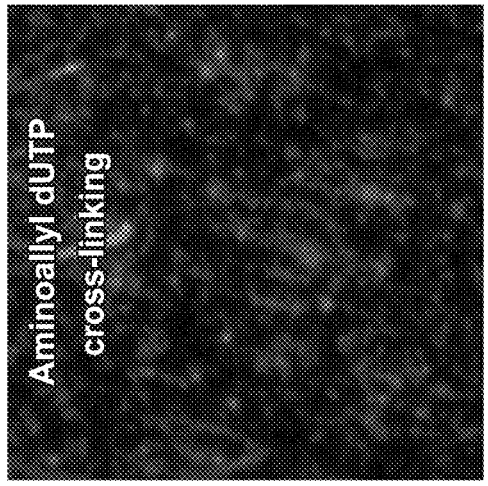
FIGS. 7C-E depict DNA amplicons with no shear stress (7C), DNA amplicons with no crosslinking and stretched out from 5 minutes of high shear stress (7D), and DNA amplicons with aminoallyl dUTP cross-linking being morphologically preserved after 5 minutes of high shear stress.
Figure 7D:
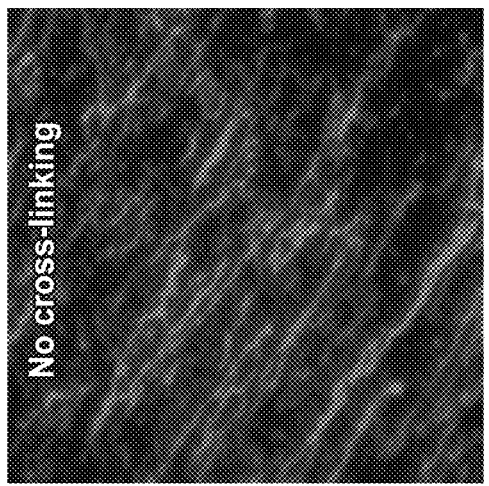
Figure 7E:
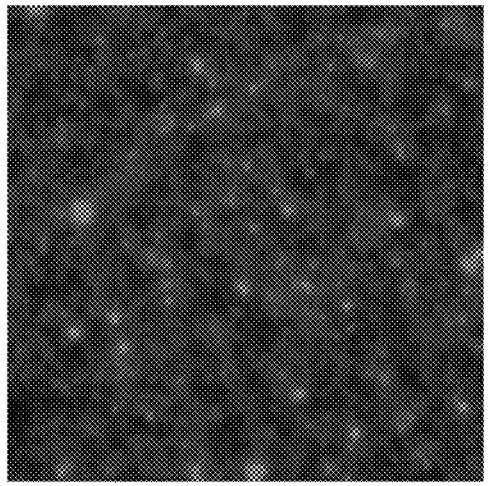
Figure 8A:
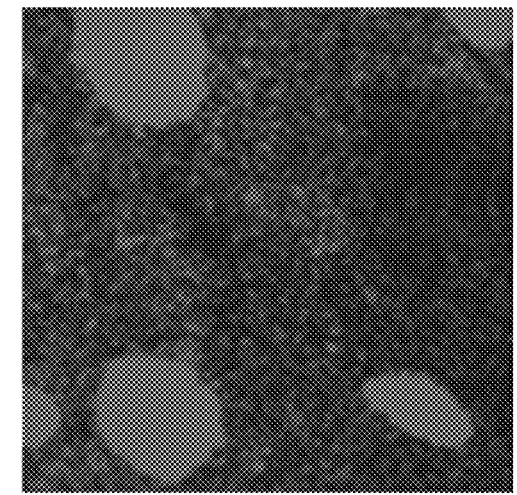
FIG. 8A depicts DNA amplicons cross-linked in fibroblasts.
Figure 8B:
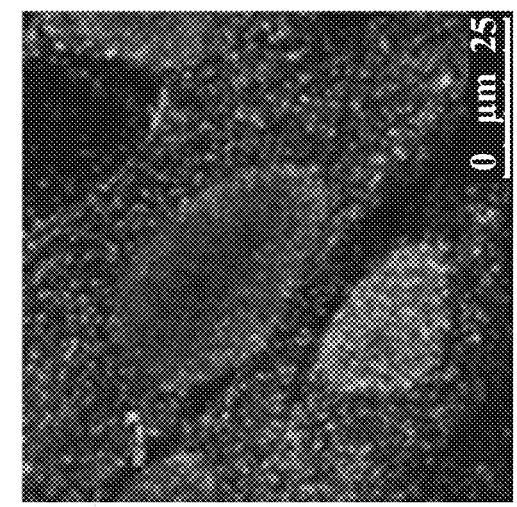
FIG. 8B depicts the results of experiments demonstrating structural integrity of a DNA amplicon matrix within a cell.
Figure 8B:
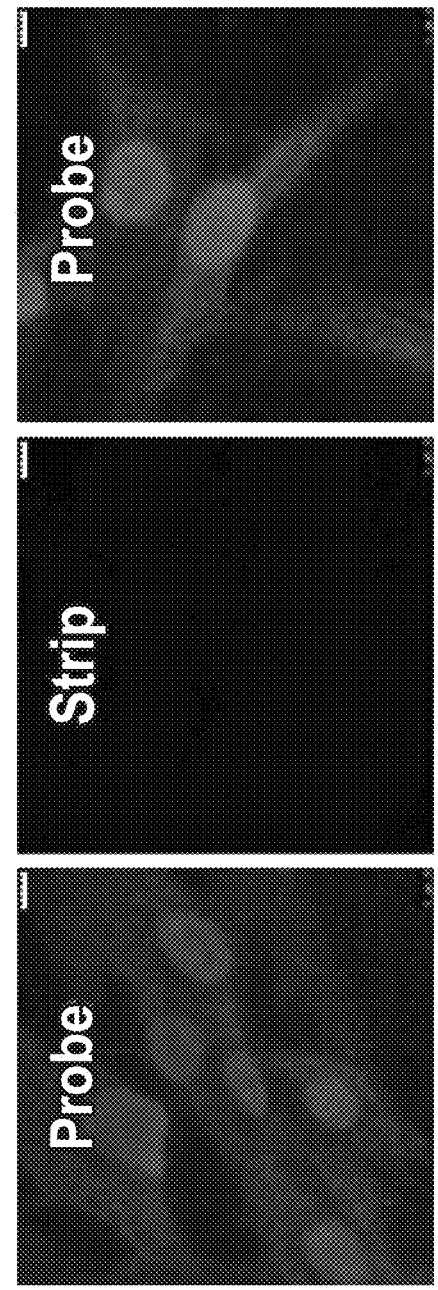
Figure 8C:
FIG. 8C depicts the results of experiments demonstrating structural integrity of a DNA amplicon matrix within a cell after numerous chemical reactions.
Figure 8C:
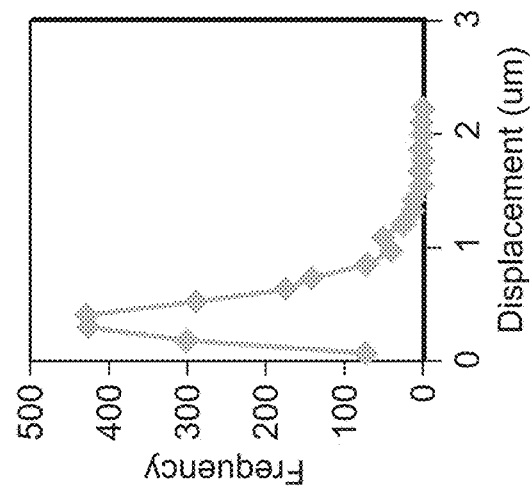
Figure 8C:
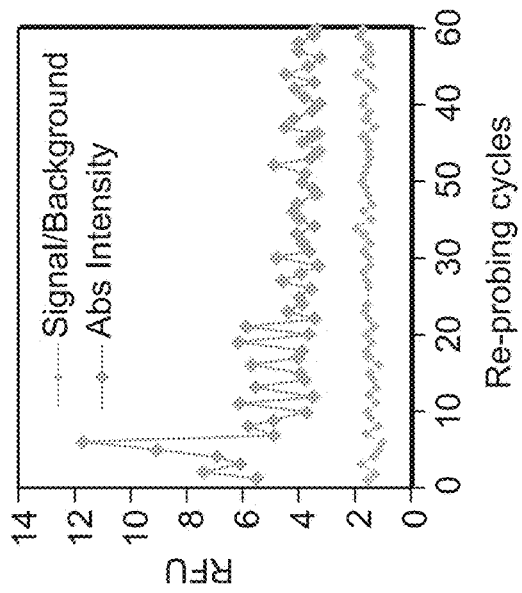
Figure 9A:
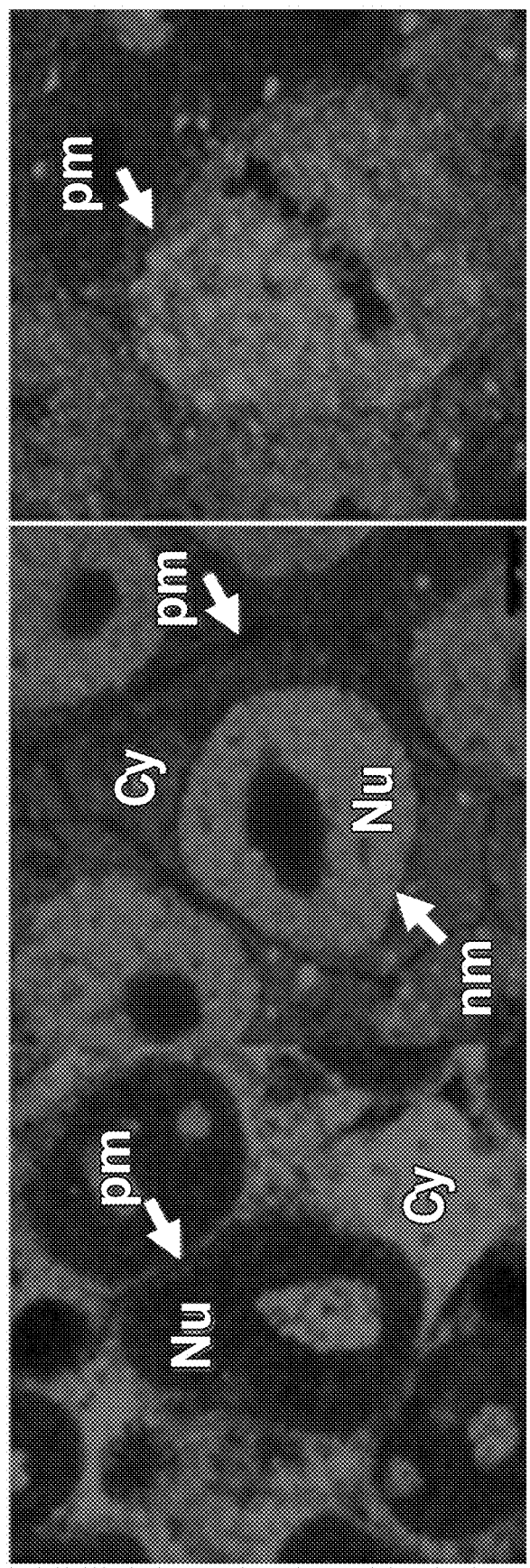
FIG. 9A depicts amplicons within pluripotent stem cells.
Figure 9B:
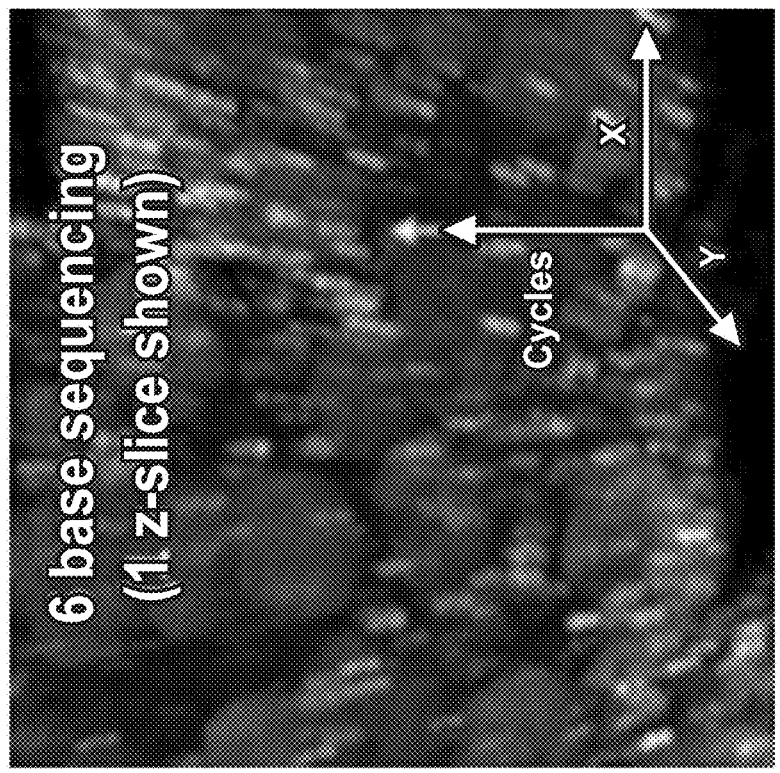
FIG. 9B depicts confocal microscope images of cells with amplicons being sequenced.
Figure 9B:
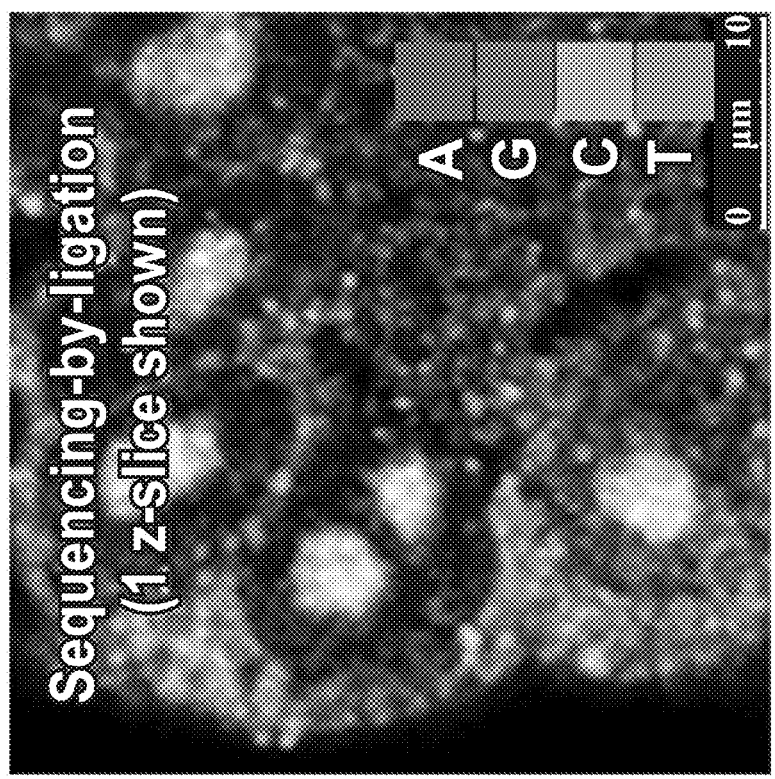
Figure 10:
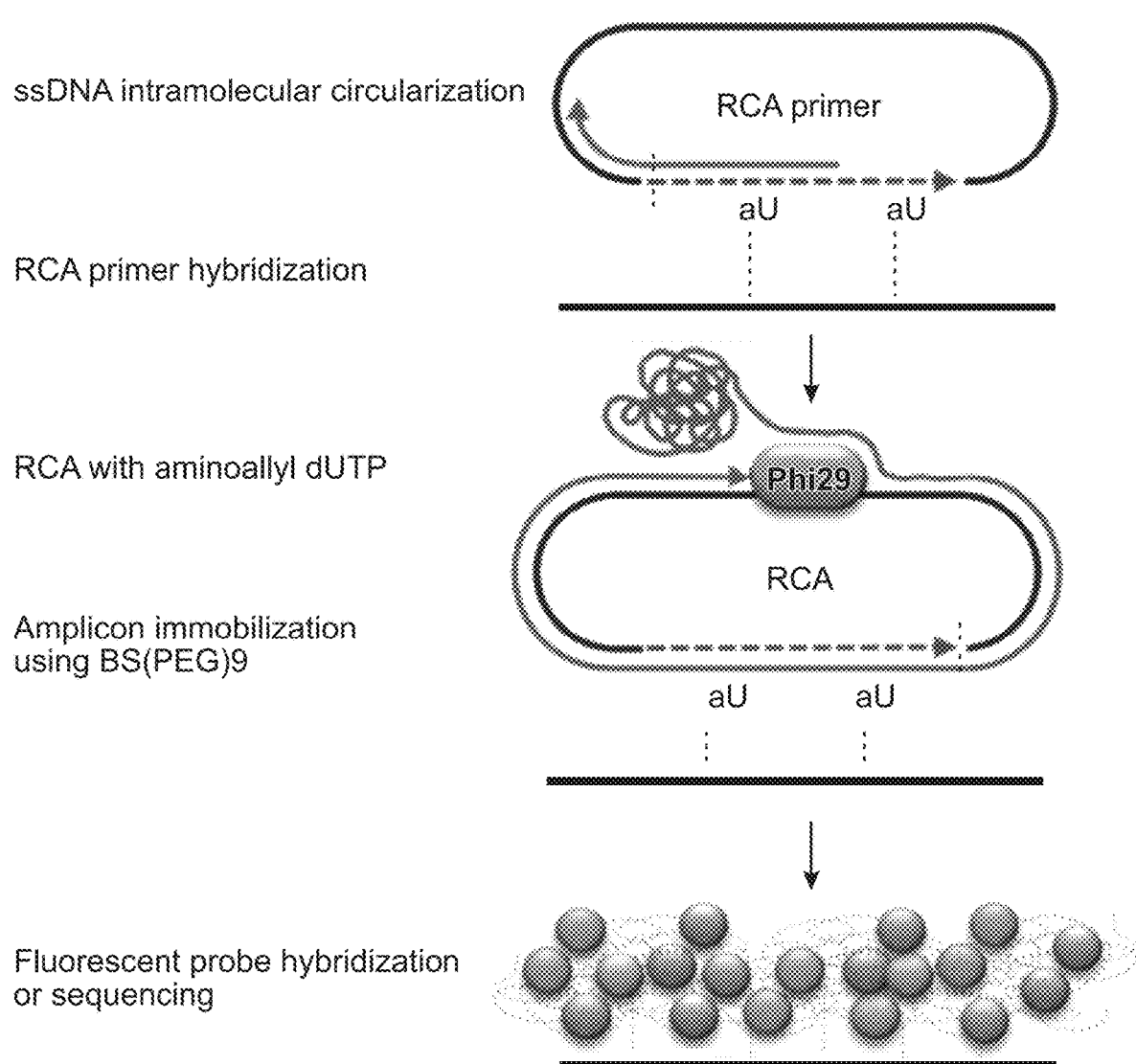
FIG. 10 depicts in schematic a process for crosslinking or copolymerizing circular DNA, amplifying the circular DNA to produce amplicons and then placing the DNA amplicons into an ordered 3D matrix using a suitable scaffold material with addressable primers that can serve as amplification primers.

As shown in FIG. 6, circular DNA, including cDNA, is first modified to incorporate a given cross-linker chemistry (i.e. aminoallyl, thiol, biotin) using modified dUTP that competes with natural dTTP. The circular DNA is then cross-linked and/or co-polymerized within a three dimensional container (i.e. cell), conforming the shape and the size of the container. Uncross-linked molecules are then washed away, and one then performs rolling circle amplification, followed by imaging (i.e. sequencing). The density, the size and the signal strength can be controlled by varying the template size, the amplification time and the detection primer sequence. The DNA amplicons can be made into an ordered 3D matrix in a suitable scaffold material with addressable primers that can serve as amplification primers.

REFERENCES

Each reference is incorporated herein by reference in its entirety for all purposes.

Drmanac, R., Sparks, A. B., Callow, M. J., Halpern, A. L., Burns, N. L., Kermani, B. G., Carnevali, P., Nazarenko, I., Nilsen, G. B., Yeung, G., et al. (2010). Human genome sequencing using unchained base reads on self-assembling DNA nanoarrays. Science 327, 78-81.

Islam, S., Kjallquist, U., Moliner, A., Zajac, P., Fan, J. B., Lonnerberg, P., and Linnarsson, S. (2011). Characterization of the single-cell transcriptional landscape by highly multiplex RNA-seq. Genome Res 21, 1160-1167.

Larsson, C., Grundberg, I., Söderberg, O., and Nilsson, M. (2010). In situ detection and genotyping of individual mRNA molecules. Nature methods 7, 395-397.

Larsson, C., Koch, J., Nygren, A., Janssen, G., Raap, A. K., Landegren, U., and Nilsson, M. (2004). In situ genotyping individual DNA molecules by target-primed rolling-circle amplification of padlock probes. Nature methods 1, 227-232.

Shendure. J., Porreca, G. J., Reppas, N. B., Lin. X., McCutcheon, J. P., Rosenbaum. A. M., Wang, M. D., Zhang, K., Mitra, R. D., and Church, G. M. (2005). Accurate multiplex polony sequencing of an evolved bacterial genome. Science 309, 1728-1732.

(c) amplifying circularized nucleic acid molecules of said plurality of circularized nucleic acid molecules in a rolling circle amplification reaction to generate a plurality of amplicons in said biological sample; and (d) using selective sequencing primers to sequence different subsets of said plurality of amplicons in said biological sample.

2. The method of claim 1, wherein (d) comprises: (i) sequencing a first subset of said plurality of amplicons in said biological sample using a first selective sequencing primer; and (ii) after sequencing said first subset of said plurality of amplicons, sequencing a second subset of said plurality of amplicons in said biological sample using a second selective sequencing primer.

3. The method of claim 1, wherein said biological sample is attached to a solid support.

4. The method of claim 3, wherein said solid support is a glass slide.

5. The method of claim 3, wherein said solid support is a flow cell.

6. The method of claim 3, wherein said biological sample is a fixed biological sample.

7. The method of claim 6, further comprising permeabilizing said fixed biological sample prior to (b).

8. The method of claim 6, further comprising contacting said fixed biological sample with proteinase K.

9. The method of claim 1, wherein said biological sample is embedded in a gel matrix.

10. The method of claim 9, wherein said biological sample is a fixed biological sample.

11. The method of claim 9, wherein said biological sample embedded in said gel matrix is attached to a solid support.

12. The method of claim 11, wherein said solid support is a glass slide.

What is claimed is:

1. A method, comprising,
   (a) providing a biological sample comprising a plurality of cells comprising a plurality of ribonucleic acid (RNA) molecules;
   (b) generating a plurality of circularized nucleic acid molecules in said biological sample, wherein each of said plurality of circularized nucleic acid molecules comprises a nucleic acid sequence corresponding to a sequence of an RNA molecule of said plurality of RNA molecules;

13. The method of claim 11, wherein said solid support is a flow cell.

14. The method of claim 9, further comprising, prior to (b), adding a polymerizable matrix forming material to said biological sample and polymerizing said polymerizable matrix forming material to embed said biological sample in said gel matrix.

15. The method of claim 1, wherein (d) comprises sequencing by synthesis.

16. The method of claim 1, wherein (d) comprises sequencing by ligation.

17. The method of claim 1, wherein (d) comprises using at least four different selective sequencing primers.

18. The method of claim 1, wherein (d) comprises using at least sixteen different selective sequencing primers.

19. A method, comprising,
- (a) providing a biological sample attached to a solid support, wherein said biological sample comprises a plurality of RNA molecules;
- (b) generating a plurality of circularized nucleic acid molecules in said biological sample, wherein each of said plurality of circularized nucleic acid molecules comprises a nucleic acid sequence corresponding to a sequence of an RNA molecule of said plurality of RNA molecules;
- (c) amplifying circularized nucleic acid molecules of said plurality of circularized nucleic acid molecules in a rolling circle amplification reaction to generate a plurality of amplicons in said biological sample; and
- (d) selectively sequencing different subpopulations of said plurality of amplicons in situ, thereby providing positional information of RNA molecules of said plurality of RNA molecules within said biological sample.

20. The method of claim 19, wherein (d) comprises, sequentially: (i) selectively sequencing a first subpopulation of said plurality of amplicons in said biological sample using a first sequencing primer and (ii) selectively sequencing a second subpopulation of said plurality of amplicons in said biological sample using a second sequencing primer.

21. The method of claim 19, wherein said solid support is a glass slide.

22. The method of claim 19, wherein said solid support is a flow cell.

23. The method of claim 19, wherein said biological sample is a fixed biological sample.

24. The method of claim 23, further comprising permeabilizing said fixed biological sample prior to (b).

25. The method of claim 23, further comprising contacting said fixed biological sample with proteinase K.

26. The method of claim 19, wherein said sequencing is sequencing by synthesis.

27. The method of claim 19, wherein said sequencing is sequencing by ligation.

28. The method of claim 19, wherein (d) comprises using at least four different sequencing primers.

29. The method of claim 19, wherein (d) comprises using at least sixteen different sequencing primers.

\* \* \* \* \*

SEQUENCE LISTING

```
Sequence total quantity: 2
SEQ ID NO: 1          moltype = DNA  length = 18
FEATURE               Location/Qualifiers
misc_feature          1..18
                      note = PCR primer
source                1..18
                      mol_type = other DNA
                      organism = synthetic construct
SEQUENCE: 1
tctcgggaac gctgaaga                                                  18

SEQ ID NO: 2          moltype = DNA  length = 19
FEATURE               Location/Qualifiers
source                1..19
                      mol_type = other DNA
                      organism = synthetic construct
misc_feature          1..19
                      note = polydT(18)V primer
SEQUENCE: 2
tttttttttt ttttttv                                                   19
```